US011991478B2

(12) United States Patent
Kamon

(10) Patent No.: US 11,991,478 B2
(45) Date of Patent: May 21, 2024

(54) MEDICAL IMAGE PROCESSING APPARATUS, MEDICAL IMAGE PROCESSING SYSTEM, MEDICAL IMAGE PROCESSING METHOD, AND PROGRAM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 618 days.

(21) Appl. No.: 17/118,535

(22) Filed: Dec. 10, 2020

(65) Prior Publication Data
US 2021/0097331 A1    Apr. 1, 2021

Related U.S. Application Data

(63) Continuation of application No. PCT/JP2019/023696, filed on Jun. 14, 2019.

(30) Foreign Application Priority Data

Jul. 9, 2018 (JP) ................................. 2018-130138

(51) Int. Cl.
*H04N 7/00* (2011.01)
*A61B 1/00* (2006.01)
(Continued)

(52) U.S. Cl.
CPC ....... *H04N 7/183* (2013.01); *A61B 1/000094* (2022.02); *A61B 1/000096* (2022.02);
(Continued)

(58) Field of Classification Search
CPC .......... H04N 7/183; H04N 5/76; G06V 10/82; G06V 10/764; G06V 2201/03;
(Continued)

(56) References Cited

U.S. PATENT DOCUMENTS 8,457,376 B2    6/2013   Kitamura et al.
10,653,295 B2   5/2020   Ebata
(Continued)

FOREIGN PATENT DOCUMENTS

CN    103547207    1/2014
CN    108135457    6/2018
(Continued)

OTHER PUBLICATIONS

"Office Action of Japan Counterpart Application", dated Jul. 30, 2021, with English translation thereof, p. 1-p. 8.
(Continued)

*Primary Examiner* — Khai M Nguyen
(74) *Attorney, Agent, or Firm* — JCIPRNET

(57) ABSTRACT

There are provided a medical image processing apparatus, a medical image processing system, a medical image processing method, and a program that allow an observer to grasp a region that contributes to classification in automatic classification of a medical image. A medical image processing apparatus includes an image acquisition unit (40) that acquires a captured image (38) generated through imaging of a living body; a classification unit (48) that classifies the captured image into two or more classes; an image generation unit (50) that generates a region image depicting a location of a region that contributes to classification performed using the classification unit in the captured image subjected to the classification performed using the classification unit; and a display signal transmission unit (44) that transmits, to a display device, a display signal representing the captured image, a classification result derived using the classification unit, and the region image. The display signal transmission unit transmits, to the display device, a display signal for displaying the region image separately from the captured image.

19 Claims, 17 Drawing Sheets

(51) Int. Cl.

| | | |
|---|---|---|
| *G06F 18/2431* | (2023.01) | |
| *G06T 7/00* | (2017.01) | |
| *G06V 10/764* | (2022.01) | |
| *G06V 10/82* | (2022.01) | |
| *H04N 5/76* | (2006.01) | |
| *H04N 7/18* | (2006.01) | |

(52) U.S. Cl.
CPC ........ *G06F 18/2431* (2023.01); *G06T 7/0012* (2013.01); *G06V 10/764* (2022.01); *G06V 10/82* (2022.01); *H04N 5/76* (2013.01); *G06T 2207/10068* (2013.01); *G06T 2207/30096* (2013.01); *G06V 2201/03* (2022.01)

(58) Field of Classification Search
CPC ........ A61B 1/000094; A61B 1/000096; G06F 18/2431; G06T 7/0012; G06T 2207/10068; G06T 2207/30096
See application file for complete search history.

(56) References Cited

U.S. PATENT DOCUMENTS

| | | | |
|---|---|---|---|
| 10,803,582 B2 | 10/2020 | Hosoi | |
| 11,087,461 B2 | 8/2021 | Ichiki | |
| 11,574,401 B2 * | 2/2023 | Aoyama | ............... A61B 1/0638 |
| 2006/0120608 A1* | 6/2006 | Luo | ........................ G06T 7/0012 |
| | | | 382/224 |
| 2007/0191677 A1 | 8/2007 | Nishimura et al. | |
| 2007/0292011 A1* | 12/2007 | Nishimura | ........... A61B 5/7264 |
| | | | 382/128 |
| 2014/0036054 A1* | 2/2014 | Zouridakis | ............ G06T 7/0012 |
| | | | 382/110 |
| 2014/0085686 A1 | 3/2014 | Ishihara | |
| 2015/0181185 A1* | 6/2015 | Ikemoto | ............... A61B 1/0684 |
| | | | 348/71 |
| 2015/0193929 A1* | 7/2015 | Ikemoto | ................. A61B 5/061 |
| | | | 382/128 |
| 2016/0174886 A1 | 6/2016 | Shiraishi | |
| 2018/0204046 A1 | 7/2018 | Bhattacharya et al. | |
| 2018/0242817 A1* | 8/2018 | Imaizumi | ................ G06T 11/60 |
| 2019/0034800 A1 | 1/2019 | Shiratani | |
| 2019/0096093 A1 | 3/2019 | Shinoda et al. | |
| 2020/0008653 A1* | 1/2020 | Kamon | ............... A61B 1/00055 |
| 2021/0000327 A1* | 1/2021 | Kitamura | ......... A61B 1/000094 |

FOREIGN PATENT DOCUMENTS

| | | | |
|---|---|---|---|
| EP | 3357406 A1 * | 8/2018 | ......... A61B 1/00009 |
| EP | 3590413 | 1/2020 | |
| EP | 3701852 | 9/2020 | |
| JP | 2007280229 | 10/2007 | |
| JP | 2008036028 | 2/2008 | |
| JP | 2010172673 | 8/2010 | |
| JP | 4615963 | 1/2011 | |
| JP | 5528255 | 6/2014 | |
| JP | 5576711 | 8/2014 | |
| JP | 2017070609 | 4/2017 | |
| JP | 2017213097 | 12/2017 | |
| JP | 2018007078 | 1/2018 | |
| WO | 2012165505 | 12/2012 | |
| WO | 2015045576 | 4/2015 | |
| WO | 2017023569 | 2/2017 | |
| WO | 2017057574 | 4/2017 | |
| WO | 201707337 | 5/2017 | |
| WO | 2017073338 | 5/2017 | |
| WO | 2017175282 | 10/2017 | |
| WO | 2018003395 | 1/2018 | |
| WO | 2018003503 | 1/2018 | |
| WO | 2018008593 | 1/2018 | |

OTHER PUBLICATIONS

"Search Report of Europe Counterpart Application", dated Aug. 10, 2021, p. 1-p. 8.

"International Search Report (Form PCT/ISA/210) of PCT/JP2019/023696," dated Sep. 10, 2019, with English translation thereof, pp. 1-5.

"Written Opinion of the International Searching Authority (Form PCT/ISA/237) of PCT/JP2019/023696," dated Sep. 10, 2019, with English translation thereof, pp. 1-10.

"Office Action of China Counterpart Application", issued on Dec. 9, 2023, with English translation thereof, p. 1-p. 14.

"Notice of Reasons for Refusal of Japan Counterpart Application No. 2023-071374", issued on Mar. 27, 2024, with English translation thereof, p. 1-p. 12.

* cited by examiner

FIG. 20
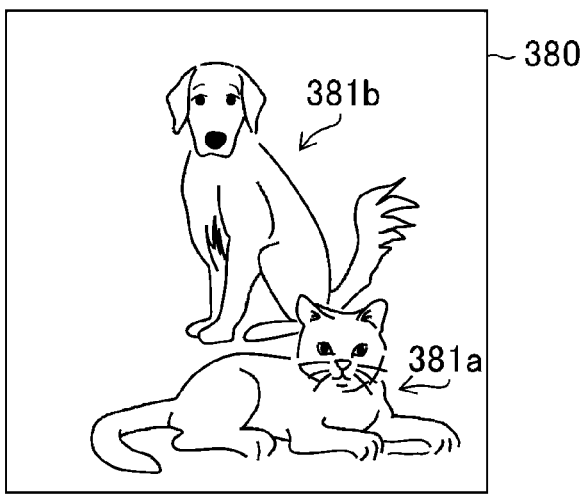
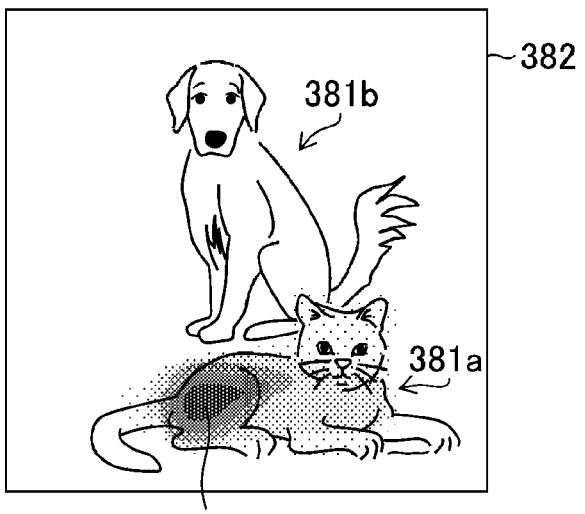
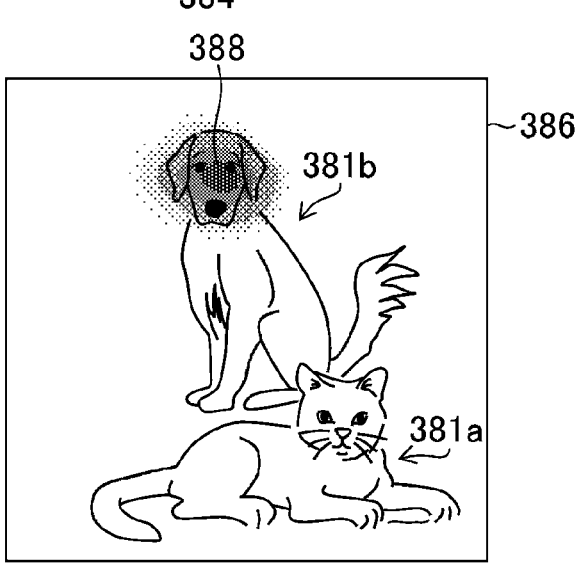

MEDICAL IMAGE PROCESSING APPARATUS, MEDICAL IMAGE PROCESSING SYSTEM, MEDICAL IMAGE PROCESSING METHOD, AND PROGRAM

CROSS-REFERENCE TO RELATED APPLICATIONS

The present application is a Continuation of PCT International Application No. PCT/JP2019/023696 filed on Jun. 14, 2019 claiming priority under 35 U.S.C § 119(a) to Japanese Patent Application No. 2018-130138 filed on Jul. 9, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing system, a medical image processing method, and a program, and more particularly to automatic classification of a lesion in a medical image.

2. Description of the Related Art

In the medical field, examinations using a modality such as an endoscope system are carried out. In recent years, there has been known a technique of analyzing medical images such as endoscopic images which are time-series images captured using an endoscope scope, automatically classifying a lesion included in the endoscopic images, and providing a classification result. Note that classification of images and discrimination of images are treated as the same concept herein.

JP5528255B describes an endoscopic image processing system that assists detection of a characteristic lesion site in an image captured with an endoscope. The endoscopic image processing system described in JP5528255B displays a dotted line so as to surround a location estimated to be a lesion site in an image displayed on a monitor when a lesion estimation function is executed.

JP2017-70609A describes an image processing system that performs texture analysis on the density of the entirety of a captured image of a blood vessel, and uses the result of the texture analysis to perform classification corresponding to pathological diagnoses of a non-tumor, an adenoma, and the like. JP2017-70609A describes an example of displaying a probability of the classification being correct.

JP4615963B describes an endoscope apparatus that removes an image inappropriate for diagnosis from among images of the inside of a body cavity captured using the endoscope apparatus.

JP5576711B describes an image processing apparatus that processes time-series images of an in-vivo lumen captured in time series using a medical observation apparatus. The image processing apparatus described in JP5576711B determines, as a specific region, a region of normal mucosa in an image constituting the time-series images. The image processing apparatus described in JP5576711B also calculates a degree of reliability of the specific region.

SUMMARY OF THE INVENTION

When the type of a lesion found in an examination of the inside of a body cavity performed using an endoscope apparatus is automatically classified using artificial intelligence (AI), the AI that performs automatic classification receives images acquired during the examination and outputs a classification result.

However, the images acquired during the examination include images that are not suitable for classification using the AI, such as an image in which a part of a lesion is not depicted because the lesion is hidden by an object although the lesion is present and an image in which a lesion is depicted but is blurred. In such a case, the AI may output an inappropriate classification result.

With the inventions described in JP5528255B, JP2017-70609A, JP4615963B, and JP5576711B, when an image that is not suitable for automatic classification described above is classified, an inappropriate classification result may be output. On the other hand, it is difficult for an observer to determine whether the classification result is appropriate.

The present invention has been made in view of such circumstances, and an object of the present invention is to provide a medical image processing apparatus, a medical image processing system, a medical image processing method, and a program that allow an observer to grasp whether classification result is appropriate in automatic classification of a medical image.

In order to accomplish the object described above, the following aspects of the invention are provided.

A medical image processing apparatus according to a first aspect includes: an image acquisition unit that acquires a captured image generated through imaging of a living body; a classification unit that classifies the captured image into two or more classes; an image generation unit that generates a region image depicting a location of a region that contributes to classification performed using the classification unit, in the captured image subjected to the classification performed using the classification unit; and a display signal transmission unit that transmits to a display device, a display signal representing the captured image, a classification result derived using the classification unit, and the region image. The display signal transmission unit transmits, to the display device, a display signal for displaying the region image separately from the captured image.

According to the first aspect, the captured image is classified into two or more classes, the region image depicting the region that contributes to the classification in the captured image is generated, and the region image is displayed separately from the captured image using the display device. This thus allows an observer to grasp a region that contributes to classification and to grasp whether the classification is appropriate.

A medical image captured using medical equipment may be used as the captured image. The medical image refers to a captured image of a living body generated using a modality such as an endoscope apparatus, a computed tomography (CT) apparatus, a magnetic resonance imaging (MRI) apparatus, or an X-ray imaging apparatus.

Predetermined medical classifications may be used as the classes.

A second aspect may be configured such that in the medical image processing apparatus according to the first aspect, the image generation unit changes a depicting manner of the region image in accordance with the classification result of the captured image.

According to the second aspect, it becomes easier to recognize the distinction between the classifications.

Examples of the depicting manner include a depicting manner using color and a depicting manner in which the location is changed. A depicting manner using both of these depicting manners may also be used.

A third aspect may be configured such that in the medical image processing apparatus according to the first or second aspect, the classification unit classifies the captured image on the basis of a feature quantity acquired from the captured image, and the image generation unit generates the region image on the basis of the feature quantity.

According to the third aspect, the region image based on the feature quantity of the captured image can be generated.

In the third aspect, the captured image may be divided into a plurality of regions, a feature quantity may be calculated for each of the regions, and a region that contributes to classification in the captured image may be identified on the basis of the features of the respective regions.

A fourth aspect may be configured such that in the medical image processing apparatus according to the first or second aspect, the classification unit employs a deep learning device that has been trained, and the image generation unit generates the region image on the basis of information of an intermediate layer of the deep learning device.

According to the fourth aspect, the region image based on the information of the intermediate layer of the trained deep learning device can be generated.

A fifth aspect may be configured such that in the medical image processing apparatus according to any one of the first to fourth aspects, the classification unit calculates, for each of a plurality of regions set in the captured image, membership degrees for the classes, and classifies the captured image on the basis of the membership degrees.

According to the fifth aspect, classification based on the membership degrees can be performed.

Examples of the membership degrees include membership probabilities for the classes and scores for the classes.

A sixth aspect may be configured such that in the medical image processing apparatus according to the fifth aspect, the image generation unit generates the region image on the basis of the membership degrees.

According to the sixth aspect, the region image based on the membership degrees can be generated.

A seventh aspect may be configured such that in the medical image processing apparatus according to any one of the first to sixth aspects, the classification unit performs exception determination for the classification based on the region image, and the display signal transmission unit transmits, to the display device, a display signal representing a result of the exception determination performed using the classification unit.

According to the seventh aspect, output of an inappropriate classification result may be suppressed for a captured image that is difficult to classify.

The display signal transmission unit may transmit, to the display device, a display signal representing a result of the exception determination instead of the classification result. The display signal transmission unit may transmit, to the display device, a display signal representing the classification result and a result of the exception determination.

An eighth aspect may be configured such that in the medical image processing apparatus according to the seventh aspect, the classification unit calculates, on the basis of the region image, a degree of reliability of the classification result derived using the classification unit, and the display signal transmission unit transmits, to the display device, a display signal representing the degree of reliability.

According to the eighth aspect, the degree of reliability of classification may be grasped.

A ninth aspect may be configured such that the medical image processing apparatus according to the eighth aspect further includes: a storage instruction acquisition unit that acquires an instruction to store the captured image; and a storage unit that stores the captured image. The storage unit associates, in storing the captured image in the storage unit in accordance with the instruction to store the captured image, at least any of the classification result, the result of the exception determination, or the degree of reliability of the classification result with the captured image.

According to the ninth aspect, the captured image and the information associated with the captured image may be used. In addition, the information associated with the captured image may be checked.

A tenth aspect may be configured such that in the medical image processing apparatus according to any one of the first to ninth aspects, the display signal transmission unit transmits to the display device, a display signal representing text information of the classification result.

According to the tenth aspect, the classification result may be grasped on the basis of the text information.

The text information may be in a language of any kind. An abbreviation may be used as the text information.

A medical image processing system according to an eleventh aspect includes: an image acquisition unit that acquires a captured image generated through imaging of a living body; a classification unit that classifies the captured image into two or more classes; an image generation unit that generates a region image depicting a location of a region that contributes to classification performed using the classification unit, in the captured image subjected to the classification performed using the classification unit; a display device that displays the captured image and the region image, and a display signal transmission unit that transmits, to the display device, a display signal representing the captured image and the region image. The display signal transmission unit transmits, to the display device, a display signal for displaying the region image separately from the captured image.

According to the eleventh aspect, substantially the same advantages as those of the first aspect can be obtained.

The eleventh aspect may be appropriately combined with any of features that are substantially the same as those specified in the second to tenth aspects. In such a case, a constituent element responsible for a process or function specified in the medical image processing apparatus can be grasped as a constituent element responsible for the corresponding process or function in the medical image processing system.

A medical image processing method according to a twelfth aspect includes: an image acquisition step of acquiring a captured image generated through imaging of a living body; a classification step of classifying the captured image into two or more classes; an image generation step of generating a region image depicting a location of a region that contributes to classification performed in the classification step, in the captured image subjected to the classification performed in the classification step; and a display signal transmission step of transmitting, to a display device, a display signal representing the captured image, a classification result derived in the classification step, and the region image. The display signal transmission step transmits, to the display device, a display signal for displaying the region image separately from the captured image.

According to the twelfth aspect, substantially the same advantages as those of the first aspect can be obtained.

The twelfth aspect may be appropriately combined with any of features that are substantially the same as those specified in the second to tenth aspects. In such a case, a constituent element responsible for a process or function specified in the medical image processing apparatus can be grasped as a constituent element responsible for the corresponding process or function in the medical image processing method.

A program according to a thirteenth aspect causes a computer to implement: an image acquisition function that acquires a captured image generated through imaging of a living body; a classification function that classifies the captured image into two or more classes; an image generation function that generates a region image depicting a location of a region that contributes to classification performed using the classification function, in the captured image subjected to the classification performed using the classification function; and a display signal transmission function that transmits, to a display device, a display signal representing the captured image, a classification result derived using the classification function, and the region image. The display signal transmission function is configured to transmit, to the display device, a display signal for displaying the region image separately from the captured image.

According to the thirteenth aspect, substantially the same advantages as those of the first aspect can be obtained.

The thirteenth aspect may be appropriately combined with any of features that are substantially the same as those specified in the second to tenth aspects. In such a case, a constituent element responsible for a process or function specified in the medical image processing apparatus can be grasped as a constituent element responsible for the corresponding process or function in the program.

According to the present invention, the captured image is classified into two or more classes, the region image depicting the region that contributes to classification in the captured image is generated, and the region image is displayed separately from the captured image using the display device. This thus allows an observer to grasp a region that contributes to classification and to grasp whether the classification is appropriate.

BRIEF DESCRIPTION OF THE DRAWINGS

FIG. 20 is a conceptual diagram of depiction based on information of an intermediate layer of the convolutional neural network;

DESCRIPTION OF THE PREFERRED EMBODIMENTS

Preferred embodiments of the present invention will be described in detail below in accordance with the accompanying drawings. The same constituent elements are denoted by the same reference signs herein, and redundant description will be appropriately omitted.

Overall Configuration of Endoscope System

Figure 1:
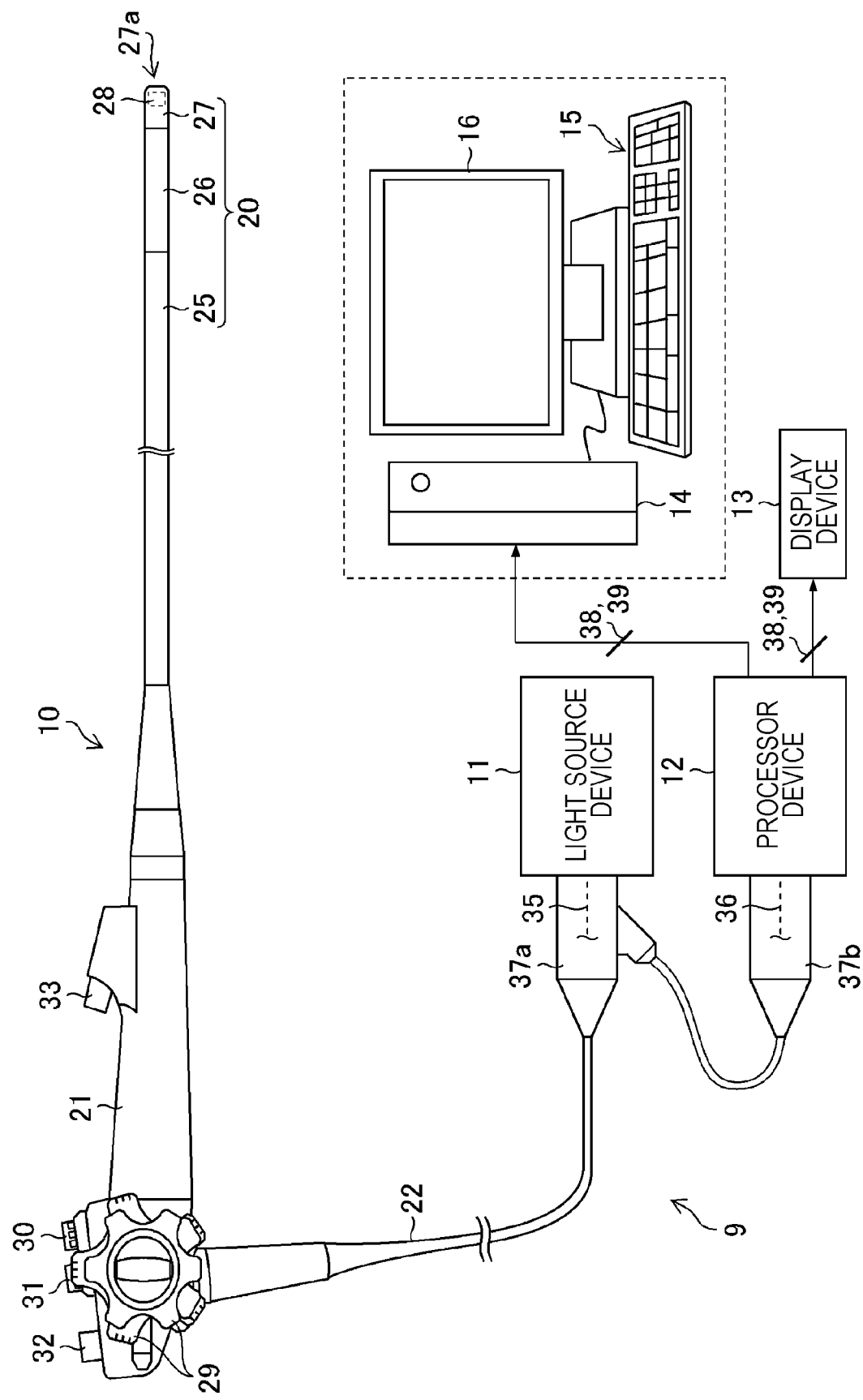
FIG. 1 is an overall configuration diagram of an endoscope system including a medical image processing apparatus according to embodiments.

FIG. 1 is an overall configuration diagram of an endoscope system including a medical image processing apparatus according to embodiments. An endoscope system 9 illustrated in FIG. 1 includes an endoscope 10, a light source device 11, a processor device 12, a display device 13, a medical image processing apparatus 14, an input device 15, and a monitor device 16.

The endoscope 10 is an electronic endoscope. The endoscope 10 is also a flexible endoscope. The endoscope 10 includes an insertion section 20, an operation section 21, and a universal cord 22. The insertion section 20 is inserted into a subject. The entire insertion section 20 is formed to have an elongated shape with a small diameter.

The insertion section 20 includes a soft part 25, a bending part 26, and a tip part 27. The soft part 25, the bending part 26, and the tip part 27 are coupled to each other to constitute the insertion section 20. The soft part 25 has flexibility sequentially from a proximal end side to a distal end side of the insertion section 20. The bending part 26 has a structure that is bendable when the operation section 21 is operated.

The tip part 27 includes an imaging optical system (not illustrated), an imaging element 28, and so on.

A CMOS imaging element or a CCD imaging element is used as the imaging element 28. CMOS is an abbreviation for complementary metal oxide semiconductor. CCD is an abbreviation for charge coupled device.

An observation window (not illustrated) is disposed on a tip surface 27a of the tip part 27. The observation window is an opening formed on the tip surface 27a of the tip part 27. A cover (not illustrated) is attached to the observation window. The imaging optical system (not illustrated) is disposed behind the observation window. Image light of a site to be observed is incident onto an imaging surface of the imaging element 28 through the observation window, the imaging optical system, and so on. The imaging element 28 images the image light of the site to be observed incident onto the imaging surface of the imaging element 28 and outputs an imaging signal. The term "imaging" used herein includes the meaning of converting light reflected off from a site to be observed into an electric signal.

The operation section 21 is coupled to the proximal end side of the insertion section 20. The operation section 21 includes various operating members to be operated by a technician. Specifically, the operation section 21 includes two types of bending operation knobs 29. The bending operation knobs 29 are used to perform an operation of bending the bending part 26. Note that the technician may also be referred to as a doctor, an operator, an observer, a user, or the like.

The operation section 21 includes an air/water supply button 30 and a suction button 31. The air/water supply button 30 is used when the technician performs an air/water supply operation. The suction button 31 is used when the technician performs a suction operation.

Figure 3:
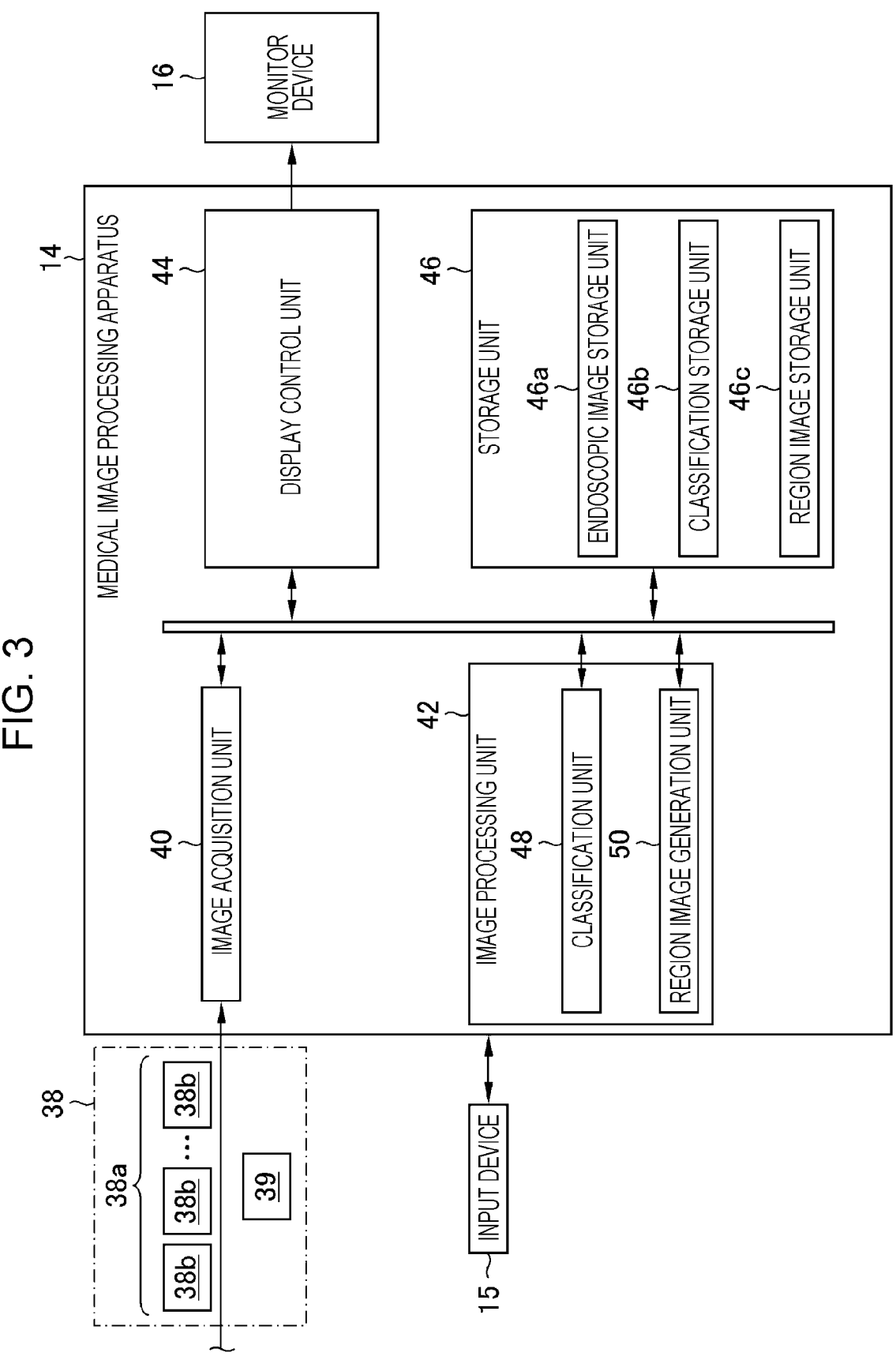
FIG. 3 is a functional block diagram of the medical image processing apparatus according to a first embodiment.

The operation section 21 includes a still image capturing instruction part 32 and a treatment tool introduction port 33. The still image capturing instruction part 32 is operated by the technician when a still image of the site to be observed is captured. The treatment tool introduction port 33 is an opening through which a treatment tool is to be inserted into a treatment tool insertion path that is inserted inside the insertion section 20. Note that illustration of the treatment tool insertion path and the treatment tool is omitted. A still image, assigned a reference sign 39, is illustrated in FIG. 3.

The universal cord 22 is a connection cord that connects the endoscope 10 to the light source device 11. The universal cord 22 includes therein a light guide 35, a signal cable 36, and a fluid tube (not illustrated), which are inserted inside the insertion section 20.

In addition, a tip part of the universal cord 22 includes a connector 37a to be connected to the light source device 11 and a connector 37b branching from the connector 37a and to be connected to the processor device 12.

When the connector 37a is connected to the light source device 11, the light guide 35 and the fluid tube (not illustrated) are inserted into the light source device 11. Consequently, necessary illumination light, water, and gas are supplied from the light source device 11 to the endoscope 10 through the light guide 35 and the fluid tube (not illustrated).

As a result, the illumination light is radiated from an illumination window (not illustrated) of the tip surface 27a of the tip part 27 toward the site to be observed. In addition, in response to an operation of pressing the air/water supply button 30, gas or water is ejected from an air/water supply nozzle (not illustrated) of the tip surface 27a of the tip part 27 toward the observation window (not illustrated) of the tip surface 27a.

When the connector 37b is connected to the processor device 12, the signal cable 36 and the processor device 12 are electrically connected to each other. Consequently, an imaging signal of the site to be observed is output from the imaging element 28 of the endoscope 10 to the processor device 12 through the signal cable 36. Also, a control signal is output from the processor device 12 to the endoscope 10 through the signal cable 36.

In the present embodiments, the flexible endoscope is described as an example of the endoscope 10. However, various types of electronic endoscopes capable of capturing a moving image of a site to be observed, such as a rigid endoscope, may be used as the endoscope 10.

The light source device 11 supplies illumination light to the light guide 35 of the endoscope 10 through the connector 37a. White light or light in a specific wavelength range is usable as the illumination light. The illumination light may be a combination of white light and light in a specific wavelength range. The light source device 11 is configured to be able to appropriately select, as the illumination light, light in a wavelength range corresponding to an observation purpose.

The white light may be light in a white wavelength range or light in a plurality of wavelength ranges. The specific wavelength range is a range narrower than the white wavelength range. As the light in the specific wavelength range, light in a single wavelength range may be used, or light in a plurality of wavelength ranges may be used. The light in the specific wavelength range may be referred to as special light.

The processor device 12 controls the operation of the endoscope 10 through the connector 37b and the signal cable 36. The processor device 12 also acquires an imaging signal from the imaging element 28 of the endoscope 10 through the connector 37b and the signal cable 36. The processor device 12 uses a predetermined frame rate to acquire an imaging signal output from the endoscope 10.

The processor device 12 generates an endoscopic image, which is an observation image of the site to be observed, on the basis of the imaging signal acquired from the endoscope 10. Herein, an endoscopic image 38 includes a moving image. The endoscopic image 38 may include the still image 39. Note that a moving image, assigned a reference sign 38a, is illustrated in FIG. 3. The endoscopic image 38 described in the embodiments is an example of a captured image.

When the still image capturing instruction part 32 of the operation section 21 is operated, the processor device 12 generates the still image 39 of the site to be observed on the basis of the imaging signal acquired from the imaging element 28 in parallel with generation of the moving image. The still image 39 may be generated to have a resolution higher than the resolution of the moving image.

When the endoscopic image 38 is generated, the processor device 12 performs image quality correction in which digital signal processing such as white balance adjustment and shading correction are used. The processor device 12 may add accessory information defined by the DICOM standard to the endoscopic image 38. Note that DICOM is an abbreviation for Digital Imaging and Communications in Medicine.

The endoscopic image 38 is an in-vivo image depicting the inside of a subject, that is, the inside of a living body. If the endoscopic image 38 is an image obtained through imaging using light in a specific wavelength range, the endoscopic image 38 is a special-light image. The processor device 12 then outputs the generated endoscopic image 38 to each of the display device 13 and the medical image processing apparatus 14. The processor device 12 may output the endoscopic image 38 to a storage device (not illustrated) via a network (not illustrated) in accordance with a communication protocol compliant with the DICOM standard. Note that a network 140 illustrated in FIG. 2 may be used as the network.

The display device 13 is connected to the processor device 12. The display device 13 displays the endoscopic image 38 transmitted from the processor device 12. The technician may perform an operation of moving the insertion section 20 forward and backward while checking the endoscopic image 38 displayed on the display device 13. Upon detecting a lesion or the like at the site to be observed, the technician may operate the still image capturing instruction part 32 to capture a still image of the site to be observed.

A computer is used as the medical image processing apparatus 14. A keyboard, a mouse, and the like connectable to the computer are used as the input device 15. The input device 15 and the computer may be connected to each other either with a cable or wirelessly. Various monitors connectable to the computer are used as the monitor device 16.

As the medical image processing apparatus 14, a diagnosis assistant apparatus such as a workstation or a server apparatus may be used. In this case, the input device 15 and the monitor device 16 are provided for each of a plurality of terminals connected to the workstation or the like. Further, as the medical image processing apparatus 14, a medical service assistant apparatus that assists creation of a medical report or the like may be used.

The medical image processing apparatus 14 acquires the endoscopic image 38 and stores the endoscopic image 38. The medical image processing apparatus 14 controls reproduction performed by the monitor device 16. Note that the term "image" used herein includes a meaning of an electric signal representing the image and a meaning of image data such as information representing the image. The term "image" used herein means at least any of an image itself or image data.

Further, the term "storing an image" can be interpreted as "saving an image". "Storing an image" used herein means "storing an image in a non-transitory manner". The medical image processing apparatus 14 may include a temporary storage memory that temporarily stores an image.

The input device 15 is used to input an operation instruction for the medical image processing apparatus 14. The monitor device 16 displays the endoscopic image 38 under the control of the medical image processing apparatus 14. The monitor device 16 may function as a display device of various kinds of information in the medical image processing apparatus 14.

The medical image processing apparatus 14 may be connected to a storage device (not illustrated) via a network (not illustrated in FIG. 1). The DICOM standard, a protocol compliant with the DICOM standard, and the like may be used as the image storage format and for the communication between apparatuses via the network.

As the storage device (not illustrated), a storage or the like that stores data in a non-transitory manner may be used. The storage device may be managed using a server apparatus (not illustrated). As the server apparatus, a computer that stores and manages various kinds of data may be used.

A configuration including the medical image processing apparatus 14 and the monitor device 16 described in the embodiments is an example of a medical image processing system.

Figure 2:
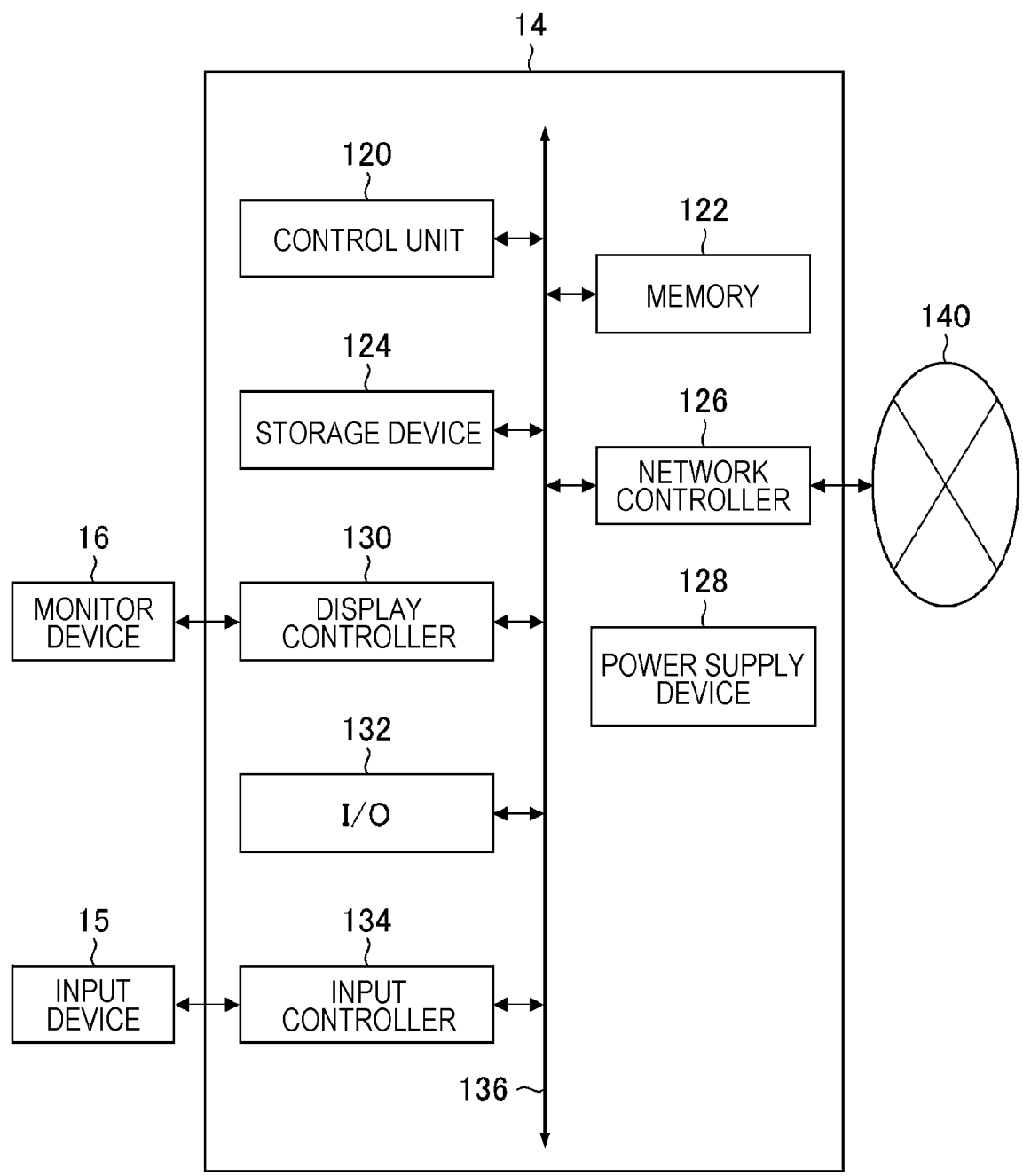
FIG. 2 is a block diagram illustrating a hardware configuration of the medical image processing apparatus.

Description of Medical Image Processing Apparatus According to First Embodiment Hardware Configuration of Medical Image Processing Apparatus FIG. 2 is a block diagram illustrating a hardware configuration of the medical image processing apparatus. The medical image processing apparatus 14 illustrated in FIG. 2 includes a control unit 120, a memory 122, a storage device 124, a network controller 126, a power supply device 128, a display controller 130, an input/output interface 132, and an input controller 134. Note that I/O illustrated in FIG. 2 represents the input/output interface 132.

The control unit 120, the memory 122, the storage device 124, the network controller 126, the display controller 130, and the input/output interface 132 are connected to each other via a bus 136 so that data communication can be performed therebetween.

Control Unit

The control unit 120 functions as an overall control unit, various calculation units, and a storage control unit of the medical image processing apparatus 14. The control unit 120 executes a program stored in a read-only memory (ROM) included in the memory 122.

The control unit 120 may download a program from an external storage device (not illustrated) via the network controller 126 and execute the downloaded program. The external storage device may be communicably connected to the medical image processing apparatus 14 via the network 140.

The control unit 120 uses, as a calculation area, a random access memory (RAM) included in the memory 122 and executes various processes in cooperation with various programs. Consequently, various functions of the medical image processing apparatus 14 are implemented.

The control unit 120 controls reading out of data from the storage device 124 and writing of data to the storage device 124. The control unit 120 may acquire various kinds of data from an external storage device via the network controller 126. The control unit 120 is capable of executing various processes such as calculations using the acquired various kinds of data.

The control unit 120 may include one processor or two or more processors. Examples of the processor include a field programmable gate array (FPGA), a programmable logic device (PLD), and so on. An FPGA and a PLD are devices whose circuit configurations are changeable after being manufactured.

Another example of the processor is an application-specific integrated circuit (ASIC). An ASIC includes a circuit configuration dedicatedly designed to execute specific processing.

The control unit 120 may use two or more processors of the same kind. For example, the control unit 120 may use two or more FPGAs or two or more PLDs. The control unit 120 may use two or more processors of different kinds. For example, the control unit 120 may use one or more FPGAs and one or more ASICs.

When the medical image processing apparatus 14 includes a plurality of control units 120, the plurality of control units 120 may be configured using a single processor. As an example of configuring the plurality of control units 120 using a single processor, there is a form in which the single processor is configured using a combination of one or more central processing units (CPUs) and software and this processor functions as the plurality of control units 120. Note that software used herein is synonymous with a program.

As another example of configuring the plurality of control units 120 using a single processor, there is a form in which a processor that implements, with a single IC chip, the functions of the entire system including the plurality of control units 120. Representative examples of the processor that implements, with a single IC chip, the functions of the entire system including the plurality of control units 120 include a system on a chip (SoC). Note that IC is an abbreviation for integrated circuit.

As described above, the control unit 120 is configured using one or more of various kinds of processors as the hardware structure.

Memory

The memory 122 includes a ROM (not illustrated) and a RAM (not illustrated). The ROM stores various programs to be executed in the medical image processing apparatus 14. The ROM stores parameters, files, and the like used for executing various programs. The RAM functions as a temporary data storage area, a work area for the control unit 120, and the like.

Storage Device

The storage device 124 stores various kinds of data in a non-transitory manner. The storage device 124 may be externally attached to the medical image processing apparatus 14. Instead of or along with the storage device 124, a large-capacity semiconductor memory device may be used.

Network Controller

The network controller 126 controls data communication between the medical image processing apparatus 14 and an external apparatus. The control of the data communication may include management of the traffic in the data communication. As the network 140 to which the medical image processing apparatus 14 is connected via the network controller 126, a known network such as a local area network (LAN) may be used.

Power Supply Device

As the power supply device 128, a large-capacity power supply device such as an uninterruptible power supply (UPS) is used. The power supply device 128 supplies power to each unit of the medical image processing apparatus 14 when the commercial power supply is cut off due to a power failure or the like.

Display Controller

The display controller 130 functions as a display driver that controls the monitor device 16 in accordance with a command signal transmitted from the control unit 120.

Input/Output Interface

The input/output interface 132 communicably connects the medical image processing apparatus 14 and an external device to each other. A communication standard such as Universal Serial Bus (USB) may be used for the input/output interface 132.

Input Controller

The input controller 134 converts the format of a signal input using the input device 15 into a format suitable for processing performed by the medical image processing apparatus 14. Information input from the input device 15 via the input controller 134 is transmitted to each unit via the control unit 120.

Note that the hardware configuration of the medical image processing apparatus 14 illustrated in FIG. 2 is merely an example. Thus, addition, deletion, and modification may be appropriately made. Note that the hardware configuration of the medical image processing apparatus 14 illustrated in FIG. 2 is also applicable to embodiments other than a first embodiment.

Description of Functional Blocks of Medical Image Processing Apparatus

FIG. 3 is a functional block diagram of the medical image processing apparatus according to the first embodiment. The medical image processing apparatus 14 includes an image acquisition unit 40, an image processing unit 42, a display control unit 44, and a storage unit 46. The image acquisition unit 40 acquires the endoscopic image 38 from the processor device 12. The image acquisition unit 40 stores the endoscopic image 38 in an endoscopic image storage unit 46a.

The image acquisition unit 40 may acquire the endoscopic image 38 from the processor device 12 via an information storage medium such as a memory card. The image acquisition unit 40 may acquire the endoscopic image 38 via the network 140 illustrated in FIG. 2.

That is, the image acquisition unit 40 may acquire the moving image 38a constituted by time-series frame images 38b. The image acquisition unit 40 may acquire the still image 39 in the case where still image capturing is performed during capturing of the moving image 38a.

The image processing unit 42 includes a classification unit 48 and a region image generation unit 50. The classification unit 48 performs automatic classification of a lesion from the endoscopic image 38. The term "classification" used herein can be read as "discrimination".

Specifically, the classification unit 48 may classify the endoscopic image 38 into a predetermined class and derive a classification result. The classification unit 48 adds class information to the frame images 38b constituting the moving image 38a at the time of automatic classification of the endoscopic image 38. The classification unit 48 may add the class information to all the frame images 38b, or may add the class information to the frame images 38b of every several frames. The classification unit 48 may add the class information to the still image 39. The class and the class information can be read as a classification result.

The classification unit 48 stores the classification result in a classification storage unit 46b in association with the frame images 38b. Table 1 below illustrates examples of classes used by the classification unit 48.

TABLE 1

| Class | Specific example |
|---|---|
| Tumor or non-tumor | Tumor, Non-tumor |
| Classification of endoscopic findings | NICE classification, JNET classification, etc. |
| Type | Hyperplastic polyp, Adenoma, Intramucosal carcinoma, Highly invasive carcinoma, Inflammatory polyp, etc. |

Note that NICE in Table 1 above is an abbreviation for NBI International Colorectal Endoscopic Classification. NBI is an abbreviation for Narrow Band Imaging. JNET is an abbreviation for The Japan NBI Expert Team.

Figure 4:
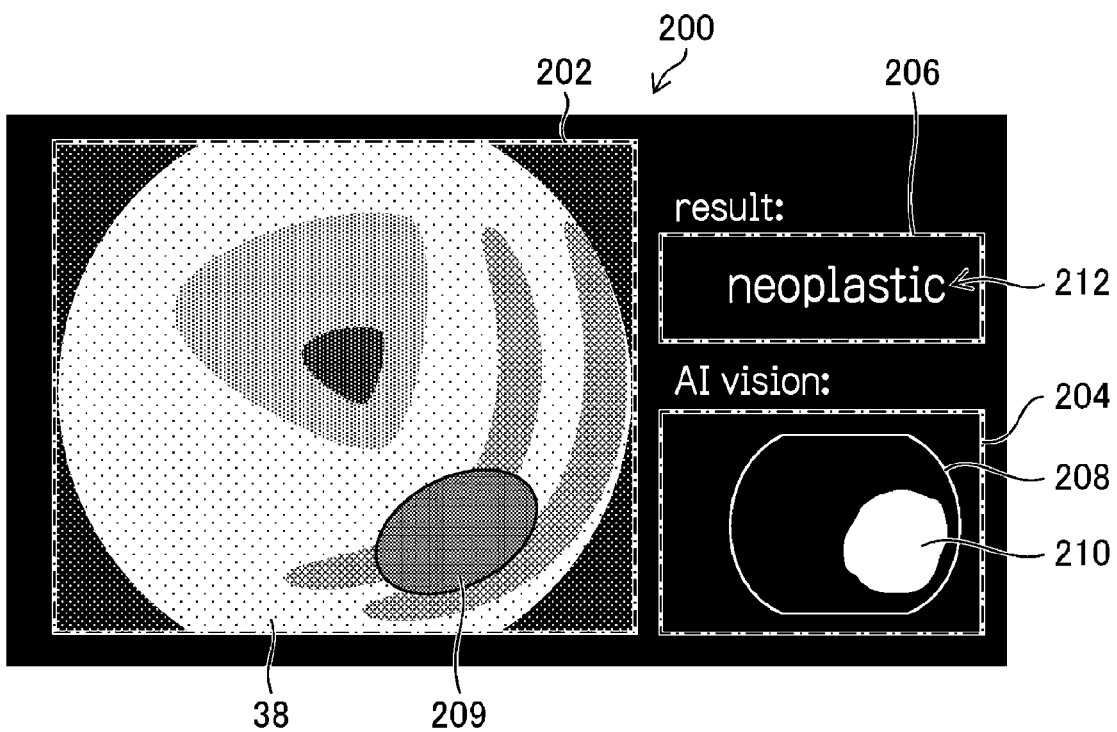
FIG. 4 is an explanatory diagram of a display screen used in the first embodiment.

The region image generation unit 50 generates a region image representing a region that contributes to classification in the endoscopic image 38. The region image generation unit 50 stores the region image in a region image storage unit 46c. The region image, assigned a reference sign 208, is illustrated in FIG. 4.

The display control unit 44 transmits, to the monitor device 16, a display control signal that causes the monitor device 16 to display the endoscopic image 38 and the region image generated using the region image generation unit 50. The display control unit 44 transmits, to the monitor device 16, a display control signal that causes the monitor device 16 to display text information representing the classification result of the endoscopic image 38 derived using the classification unit 48. The display control unit 44 described in the embodiments is an example of a display signal transmission unit.

The monitor device 16 displays the endoscopic image 38, the region image, and the text information representing the classification result in the same screen. The monitor device 16 displays the endoscopic image 38 and the region image in different regions in the screen. Text information, assigned a reference sign 212, representing the classification result is illustrated in FIG. 4. Details of the screen displayed using the monitor device 16 will be described later.

The storage unit 46 includes the endoscopic image storage unit 46a, the classification storage unit 46b, and the region image storage unit 46c. The endoscopic image storage unit 46a stores the endoscopic image 38 acquired using the image acquisition unit 40.

The image processing unit 42 reads out the endoscopic image 38 stored in the endoscopic image storage unit 46a and performs image processing on the endoscopic image 38. The display control unit 44 reads out the endoscopic image 38 stored in the endoscopic image storage unit 46a and causes the monitor device 16 to display the endoscopic image 38.

The classification storage unit 46b stores the class of the endoscopic image 38 classified using the classification unit 48 in association with the endoscopic image 38. Specifically, the classification storage unit 46b stores, in association with the frame image 38b, the class of the frame image 38b constituting the moving image 38a. The display control unit 44 reads out the classification result from the classification storage unit 46b and causes the monitor device 16 to display the text information or the like representing the classification result.

The region image storage unit 46c stores the region image generated using the region image generation unit 50. The display control unit 44 reads out the region image from the region image storage unit 46c and causes the monitor device 16 to display the region image.

One or more storage elements may be used as the storage unit 46 illustrated in FIG. 3. That is, the storage unit 46 may include three storage elements corresponding to the endoscopic image storage unit 46a, the classification storage unit 46b, and the region image storage unit 46c, respectively. A plurality of storage elements may be used as each of the endoscopic image storage unit 46a, the classification storage unit 46b, and the region image storage unit 46c. Furthermore, two or all of the endoscopic image storage unit 46a, the classification storage unit 46b, and the region image storage unit 46c may be configured using a single storage element.

Description of Display Screen Displayed on Monitor Device
Description of Region Image FIG. 4 is an explanatory diagram of a display screen used in the first embodiment. A display screen 200 illustrated in FIG. 4 includes an endoscopic image display area 202, a region image display area 204, and a classification result display area 206.

The endoscopic image display area 202 is an area in which the endoscopic image 38 is displayed. The still image 39 may be displayed in the endoscopic image display area 202. The endoscopic image 38 and the still image 39 may be displayed in a switching manner in the endoscopic image display area 202. A reference sign 209 denotes a classification contribution region 209 which is a region that contributes to classification of the endoscopic image 38. FIG. 4 schematically illustrates the classification contribution region 209.

The region image 208 is displayed in the region image display area 204. In the region image 208, a classification contribution corresponding region 210 is displayed with highlight. The classification contribution corresponding region 210 is a region, in the region image 208, corresponding to the classification contribution region 209.

The text information 212 representing the classification result is displayed in the classification result display area 206. FIG. 4 illustrates an example in which "neoplastic", which is the English notation for a tumor, is displayed as the text information 212 in the classification result display area 206. Note that the text information 212 may be in a language of any kind. That is, Japanese notation or foreign language notation other than English may be used for the text information 212. An abbreviation may also be used for the text information 212.

Figure 5:
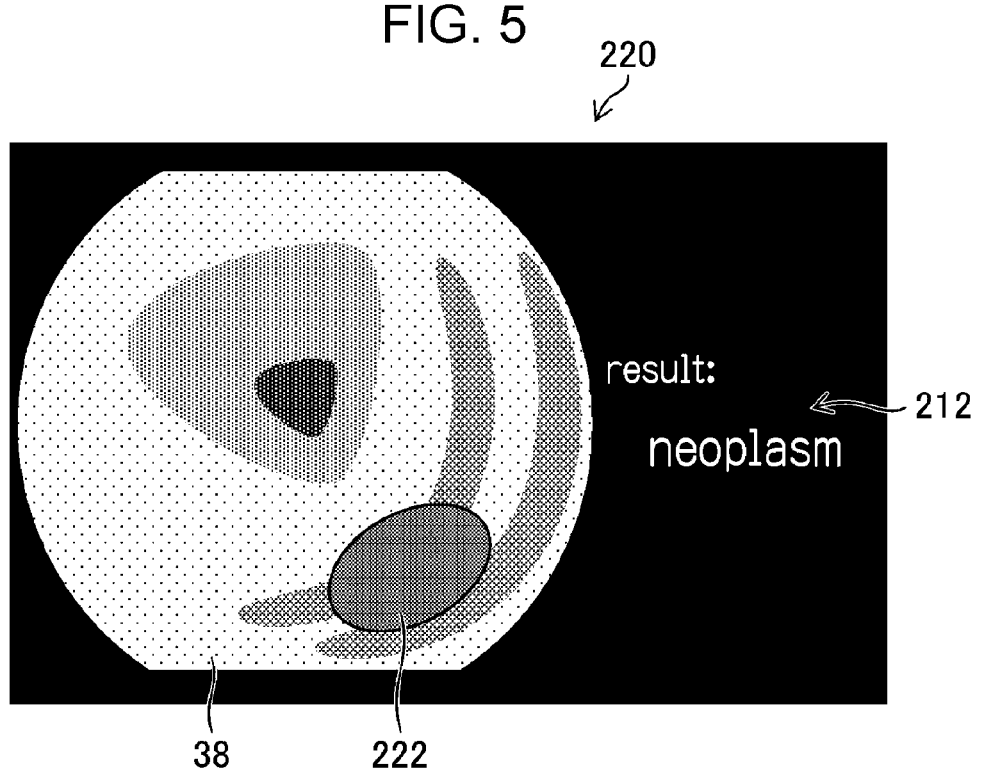
FIG. 5 is an explanatory diagram of a display screen according to a comparative example.

FIG. 5 is an explanatory diagram of a display screen according to a comparative example. A comparative screen 220 displays the result of automatic classification, and indicates an example in which a tumor 222 is found from the endoscopic image 38 and the endoscopic image 38 is classified to the tumor. The endoscopic image 38 and the text information 212 representing the classification result are displayed in the comparative screen 220. Note that FIG. 5 schematically illustrates the tumor 222.

The text information 212 representing the classification result is displayed in the comparative screen 220 illustrated in FIG. 5. However, when the endoscopic image 38 is difficult to classify, an incorrect classification result may be output. On the other hand, the region image 208 corresponding to the endoscopic image 38 is displayed in the display screen 200 illustrated in FIG. 4, and the classification contribution corresponding region 210 is displayed in the region image 208. This allows an observer to visually grasp which region in the endoscopic image 38 the classification unit 48 performs classification on the basis of. In addition, the region image 208 may serve as an index of the reliability of the classification result.

Figure 6:
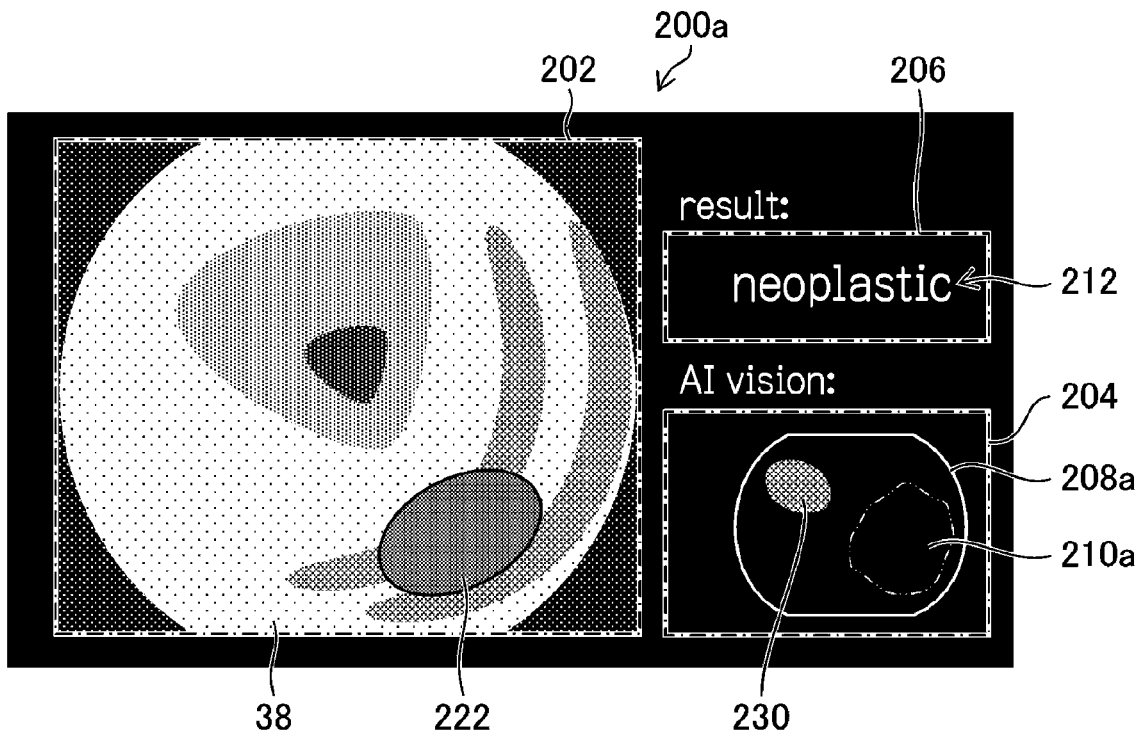
FIG. 6 is an explanatory diagram of a display screen displayed when the reliability of a classification result is low.

FIG. 6 is an explanatory diagram of a display screen displayed when the reliability of the classification result is low. A display screen 200a illustrated in FIG. 6 corresponds to an example of the case where the classification result is incorrect and the classification is performed on the basis of a region different from the tumor 222 in the endoscopic image 38.

In a region image 208a illustrated in FIG. 6, a region 230 different from a region to be set as a classification contribution corresponding region 210a is displayed as the classification contribution corresponding region.

Figure 7:
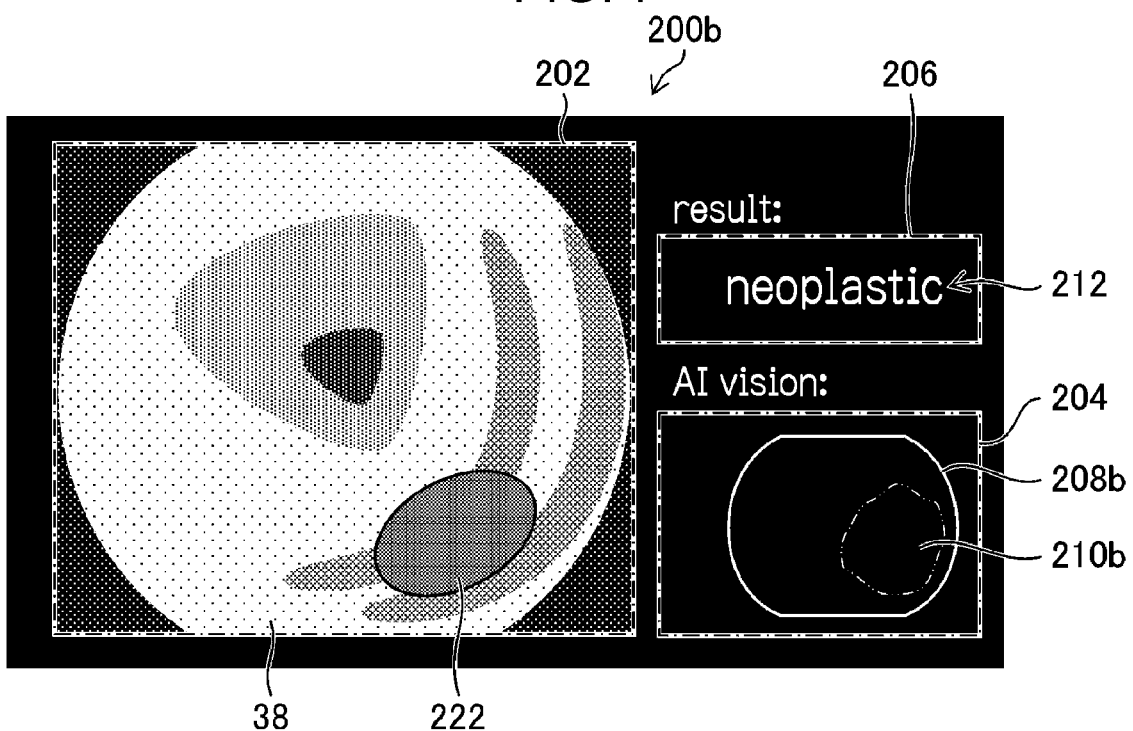
FIG. 7 is an explanatory diagram of a display screen of another example displayed when the reliability of the classification result is low.

FIG. 7 is an explanatory diagram of a display screen of another example displayed when the reliability of the classification result is low. A display screen 200b illustrated in FIG. 7 corresponds to an example displayed in the case where the tumor 222 in the endoscopic image 38 fails to be found.

In a region image 208b illustrated in FIG. 7, a region 210b to be set as the classification contribution corresponding region is not displayed. When the display screen 200b illustrated in FIG. 7 is displayed, it is considered that the classification unit 48 fails to find a target to be classified due to reasons such as the tumor 222 being blurred and the size of the tumor 222 being small.

In such a case, the operator operates the endoscope 10 illustrated in FIG. 1 to adjust the focus or to display the lesion and a peripheral region of the lesion in an enlarged manner. This allows the classification unit 48 to perform classification correctly. That is, displaying the region image 208 together with the endoscopic image 38 may serve as a suggestion that prompts the operator to perform an operation that causes the classification unit 48 to derive the correct classification result.

In the present embodiment, the example in which the endoscopic image display area 202 and the region image display area 204 are displayed in the display screen 200 displayed on the single monitor device 16 has been described. Alternatively, the display screen 200 including the endoscopic image display area 202 may be displayed on one of two monitor devices, and the display screen 200 including the region image display area 204 may be displayed on the other monitor device.

In addition, the endoscopic image display area 202 and the region image display area 204 may be displayed in the single display screen 200 displayed on the single monitor device 16 so as to be switched in a time division manner. Further, the region image display area 204 may be displayed to be superimposed on the endoscopic image display area 202. For example, the region image display area 204 may be displayed to be superimposed, at a location where observation of the endoscopic image 38 is not hindered in the endoscopic image display area 202, such as a lower left corner of the endoscopic image display area 202 illustrated in FIG. 7.

The observer tends to dislike movement of the viewpoint because the observer observes the endoscopic image while performing a precise operation. When the region image display area 204 is displayed to be superimposed on the endoscopic image display area 202, the endoscopic image display area 202 and the region image display area 204 in the display screen 200b are arranged at closer locations. This effectively reduces movement of the viewpoint of the observer.

Figure 8:
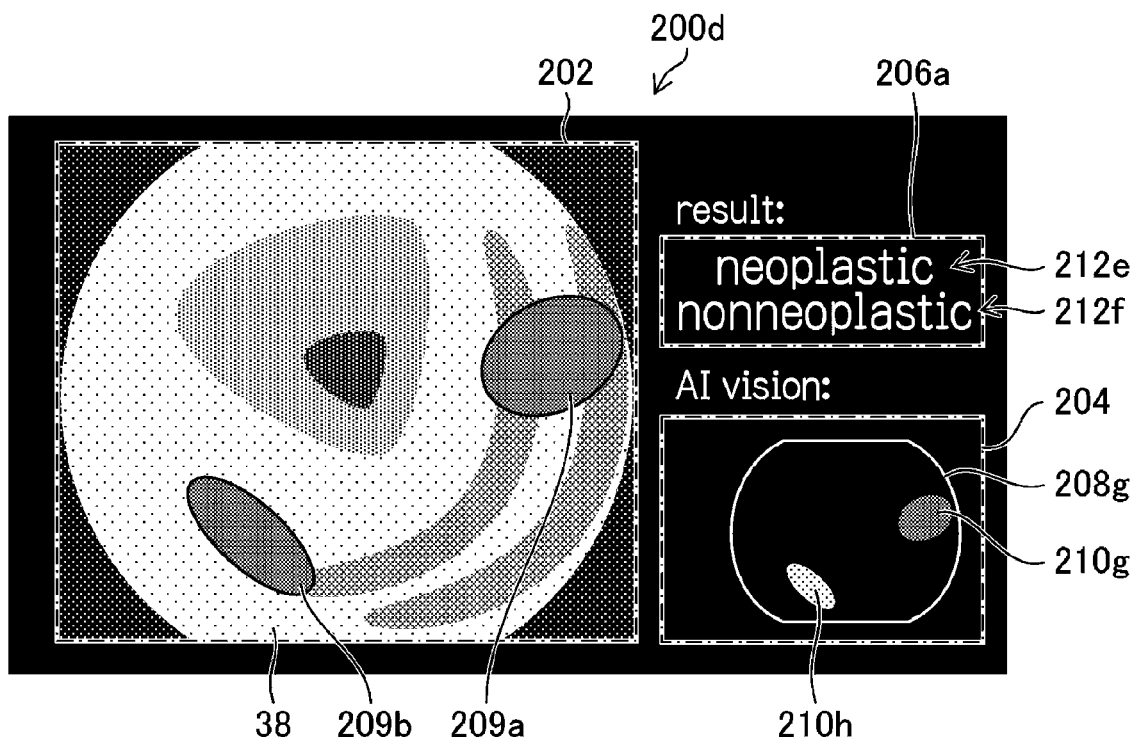
FIG. 8 is an explanatory diagram of a display screen displayed when a plurality of lesions are present.

FIG. 8 is an explanatory diagram of a display screen displayed when a plurality of lesions are present. In a display screen 200d illustrated in FIG. 8, a first classification contribution region 209a and a second classification contribution region 209b are extracted for the plurality of lesions that are present in the endoscopic image 38.

In a region image 208g, a first classification contribution corresponding region 210g corresponding to the first classification contribution region 209a and a second classification contribution corresponding region 210h corresponding to the second classification contribution region 209b are displayed. A display manner is used that enables the first classification contribution corresponding region 210g and the second classification contribution corresponding region 210h to be distinguished from each other.

Further, in a classification result display area 206a of the display screen 200d, first text information 212e representing a first classification result for the first classification contribution corresponding region 210g and second text information 212f representing a second classification result for the second classification contribution corresponding region 210h are displayed.

When lesions of different classifications, such as a non-neoplastic lesion and a neoplastic lesion, are present, it is difficult for a system that outputs one classification result from the endoscopic image 38 to return an appropriate classification result. In contrast, the medical image processing apparatus 14 according to the present embodiment uses the display manners for the respective classifications in the region image 208g as illustrated in FIG. 8 to depict the first classification contribution region 209a and the second classification contribution region 209b. This enables appropriate classification results to be obtained even when a plurality of lesions are present in the endoscopic image 38 and the classifications of the plurality of lesions are different from each other.

Description of Display of Classification Result

Figure 9:
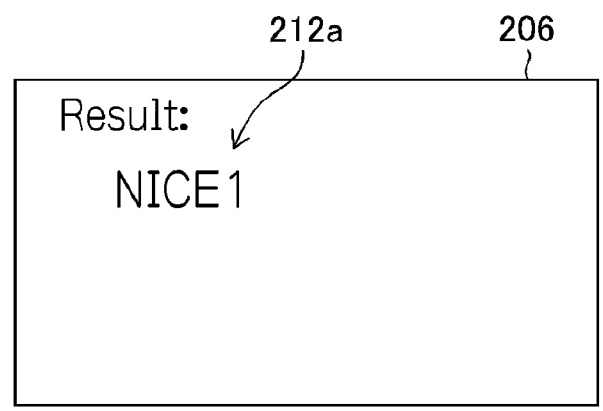
FIG. 9 is an explanatory diagram of a display example of a classification result.

FIG. 9 is an explanatory diagram of a display example of a classification result. FIG. 9 illustrates an example in which a specific class is displayed as a classification result. Text information 212a illustrated in FIG. 9 indicates that the classification result is NICE 1.

Figure 10:
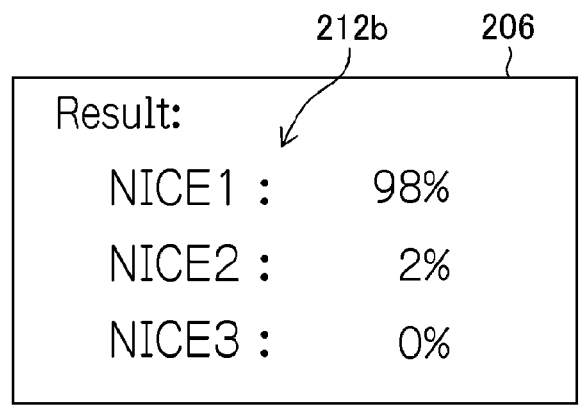
FIG. 10 is an explanatory diagram of an example of displaying membership probabilities as classification results.

FIG. 10 is an explanatory diagram of an example of displaying membership probabilities as the classification results. FIG. 10 illustrates an example in which the membership probabilities for the respective classes are displayed as the classification results. Text information 212b illustrated in FIG. 10 indicates that the membership probability for NICE 1 is 98%, the membership probability for NICE 2 is 2%, and the membership probability for NICE 3 is 0%.

The text information 212b illustrated in FIG. 10 may be text indicating that the membership probability for NICE 1 is 98% alone. The text information 212b illustrated in FIG. 10 may be text indicating that the membership probability for NICE 1 is 98% and the membership probability for NICE 2 is 2%.

Figure 11:
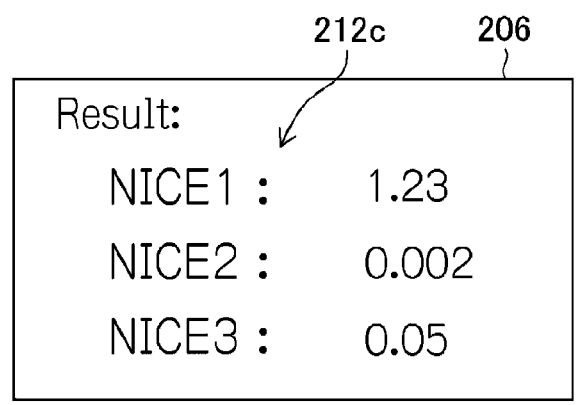
FIG. 11 is an explanatory diagram of an example of displaying scores as classification results.

FIG. 11 is an explanatory diagram of an example of displaying scores as the classification results. FIG. 11 illustrates an example in which the scores for the respective classes are displayed as the classification results. Text information 212c illustrated in FIG. 11 indicates that the score for NICE 1 is 1.23, the score for NICE 2 is 0.002, and the score for NICE 3 is 0.05. The membership probabilities illustrated in FIG. 10 and the scores illustrated in FIG. 11 are examples of membership degrees for classes.

Procedure of Medical Image Processing Method

Figure 12:
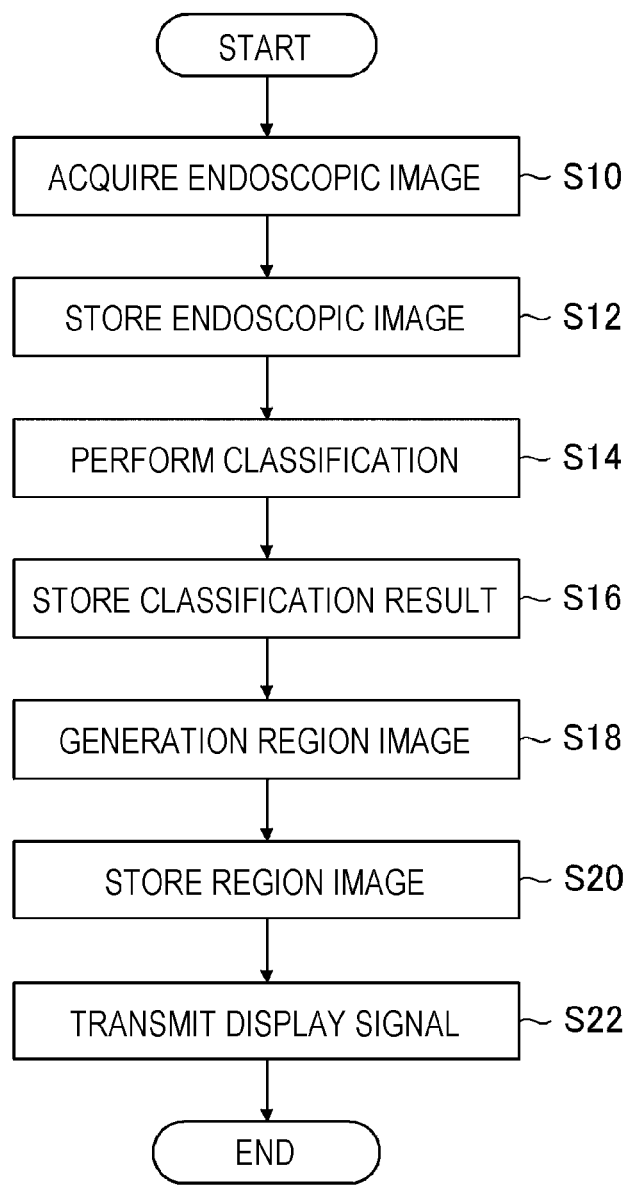
FIG. 12 is a flowchart illustrating a procedure of a medical image processing method.

FIG. 12 is a flowchart illustrating a procedure of a medical image processing method. In an endoscopic image acquisition step S10, the image acquisition unit 40 illustrated in FIG. 3 acquires the endoscopic image 38. In an endoscopic image storage step S12, the image acquisition unit 40 stores the endoscopic image 38 acquired in the endoscopic image acquisition step S10 in the endoscopic image storage unit 46a.

In a classification step S14, the classification unit 48 classifies the endoscopic image 38 into a predetermined class. In a classification result storage step S16, the classification unit 48 stores the classification result derived in the classification step S14 in the classification storage unit 46b.

In a region image generation step S18, the region image generation unit 50 generates a region image such as the region image 208 illustrated in FIG. 4 on the basis of the classification result. In a region image storage step S20, the region image generation unit 50 stores the region image generated in the region image generation step S18 in the region image storage unit 46c.

In a display signal transmission step S22, the display control unit 44 transmits a display signal to the monitor device 16. The display signal transmitted from the display control unit 44 to the monitor device 16 includes a display signal representing the endoscopic image 38 and the region image 208. The display signal transmitted from the display control unit 44 to the monitor device 16 may include a display signal representing the classification result.

Modifications of Display Screen

Modification of Region Image

Figure 13:
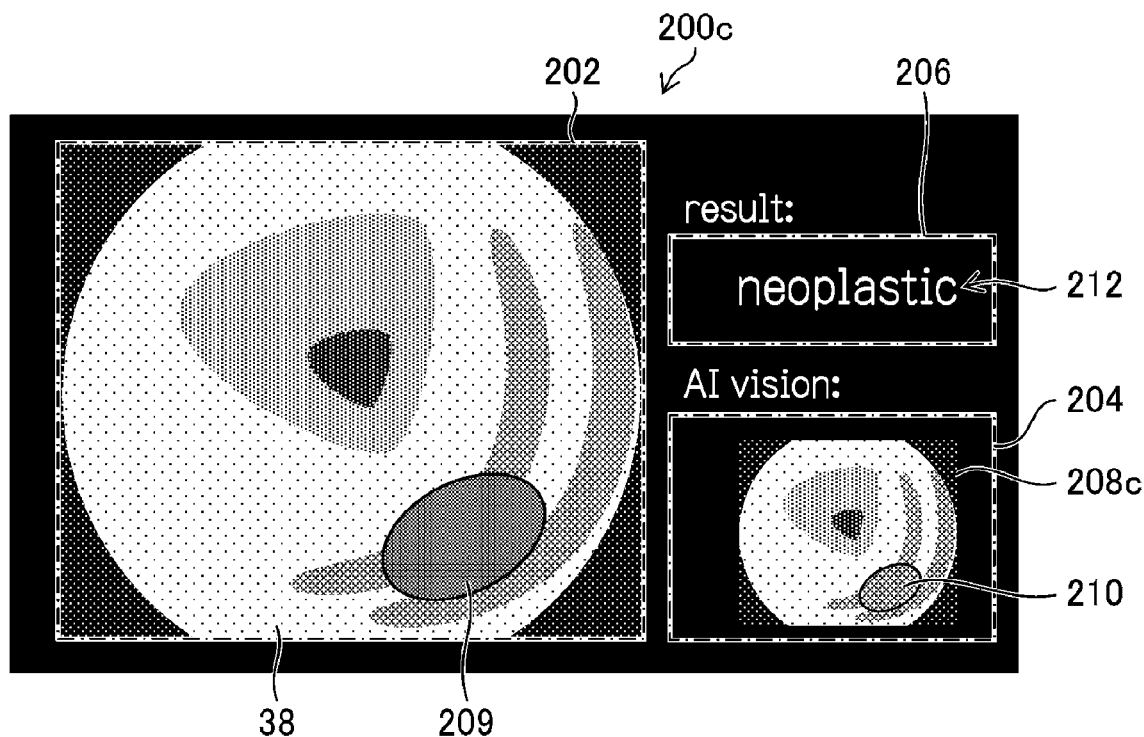
FIG. 13 is an explanatory diagram of a display screen according to a modification of a region image.

FIG. 13 is an explanatory diagram of a display screen according to a modification of a region image. In a display screen 200c illustrated in FIG. 13, a reduced-size image of the endoscopic image 38 is combined in the background of a region image 208c. That is, in the region image 208c, the classification contribution corresponding region 210 is displayed to be superimposed on the reduced-size endoscopic image 38. The reduced-size image of the endoscopic image 38 may have a lower resolution than the endoscopic image 38.

Modifications of Classification Result

Figure 14:
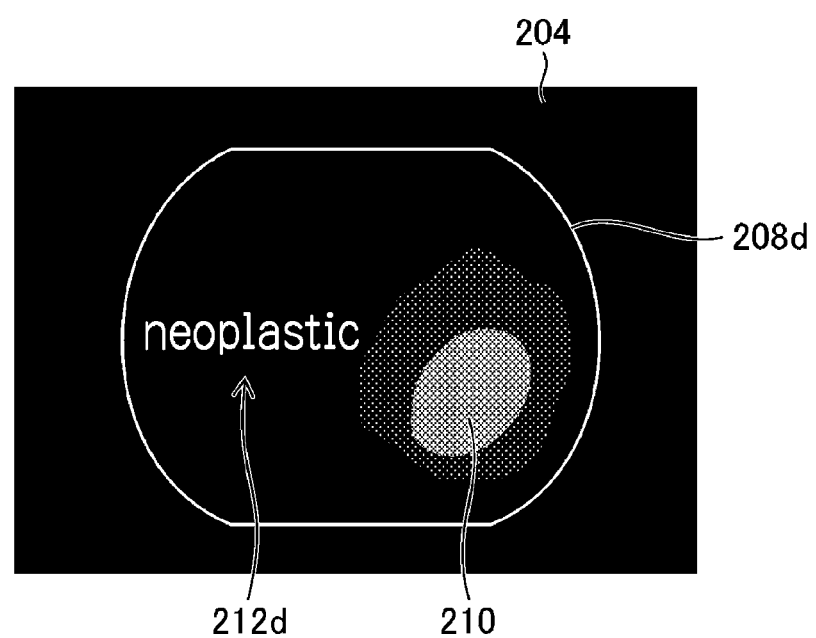
FIG. 14 is an explanatory diagram of a display screen according to a first modification of the classification result.

FIG. 14 is an explanatory diagram of a display screen according to a first modification of the classification result. In a region image 208d illustrated in FIG. 14, text information 212d representing the classification result is displayed to be superimposed. In the region image 208d, emphasis on the text information 212d such as changing the color of the text information 212d from the color of the classification contribution corresponding region 210 may be used.

Figure 15:
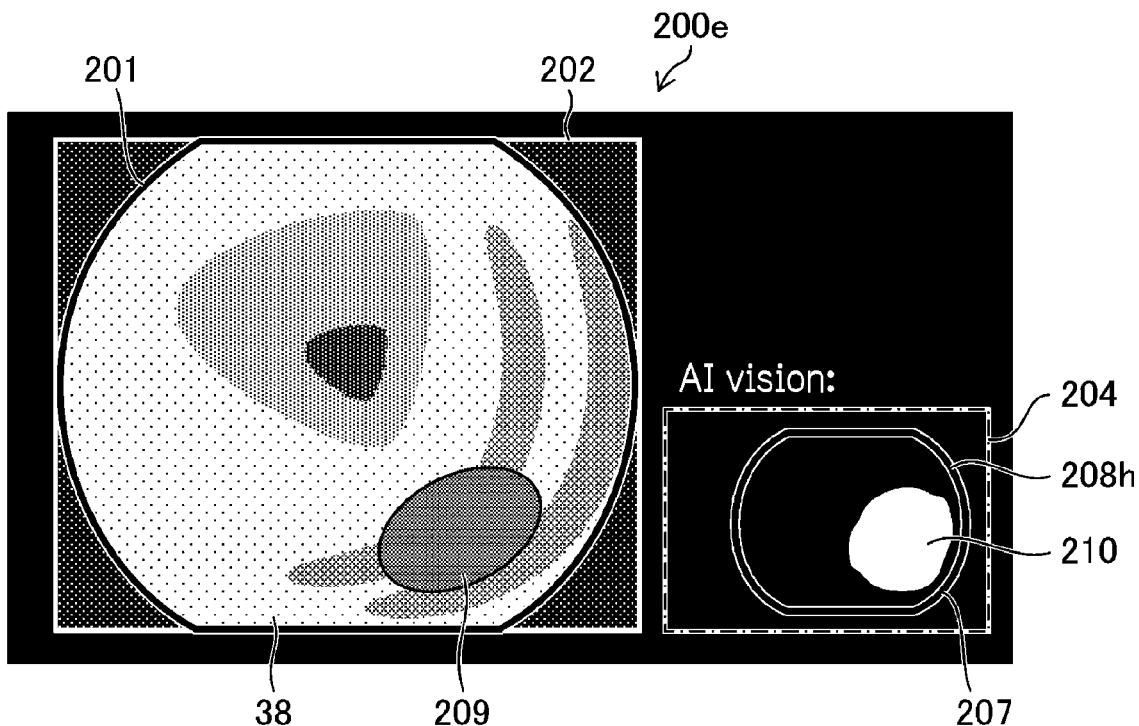
FIG. 15 is an explanatory diagram of a display screen according to a second modification of the classification result.

FIG. 15 is an explanatory diagram of a display screen according to a second modification of the classification result. In a display screen 200e illustrated in FIG. 15, a frame 201 of the endoscopic image 38 and a frame 207 of a region image 208h are colored in accordance with the classification result. Note that the frame 201 alone may be colored, or the frame 207 alone may be colored. That is, in the display screen 200e, at least any of the frame 201 of the endoscopic image 38 or the frame 207 of the region image 208h is colored in accordance with the classification result.

Since the observer observes the endoscopic image while performing a precise operation, there is a concern that the movement of the viewpoint of the observer, the visual recognition of the text information by the observer, and the like may adversely affect the operation performed by the observer. In contrast, the operator who views the display screen 200e illustrated in FIG. 15 may grasp the classification result with almost no movement of the viewpoint.

In addition to coloring the frame 201 or the like in accordance with the classification result, the medical image processing apparatus 14 may be configured such that the frame 201 or the like is colored in the case where the classification result is a specific classification such as a tumor and the frame 201 or the like is not colored in the case where the classification result is another classification. Alternatively, the medical image processing apparatus 14 may color the frame 201 or the like in the case of exceptional determination (described later), or may change the color in accordance with the degree of reliability in the case where the display is changed in accordance with the degree of reliability.

The configuration of changing the color may include a configuration of changing the density of the same color. For example, deep red may be used if the endoscopic image 38 is classified into a tumor, and light red may be used if the endoscopic image 38 is classified into a non-tumor. An object to be colored is not limited to the frame 201 or the like. A region other than the frames 201 and 207 may be colored. Furthermore, a non-color-based display manner such a display manner using a symbol can be used as long as the display manner makes the movement of the viewpoint of the operator less and makes it easier for the operator to grasp the classification result than the text information.

Other Modifications

The display manner of the region image may be changed in accordance with the classification result. For example, in a case where the endoscopic image 38 is classified into two classes of a tumor and a non-tumor, the color used in the case of the tumor may be changed from the color used in the case of the non-tumor. In such an example, red may be used if the endoscopic image 38 is classified into the tumor, and blue may be used if the endoscopic image 38 is classified into the non-tumor.

Alternatively, the display screen may be configured such that the plurality of region image display areas 204 are displayable, and the location of the region image 208 may be changed in accordance with the classification result. For example, in a display screen in which two region image display areas 204 vertically displayable, the upper region image display area 204 may be used if the endoscopic image 38 is classified into the tumor, and the lower region image display area 204 may be used if the endoscopic image 38 is classified into the non-tumor. The modifications of the display screen described above may assist the visibility of the operator. The display manner according to the classification result described in the embodiments is an example of a depicting manner.

Figure 16:
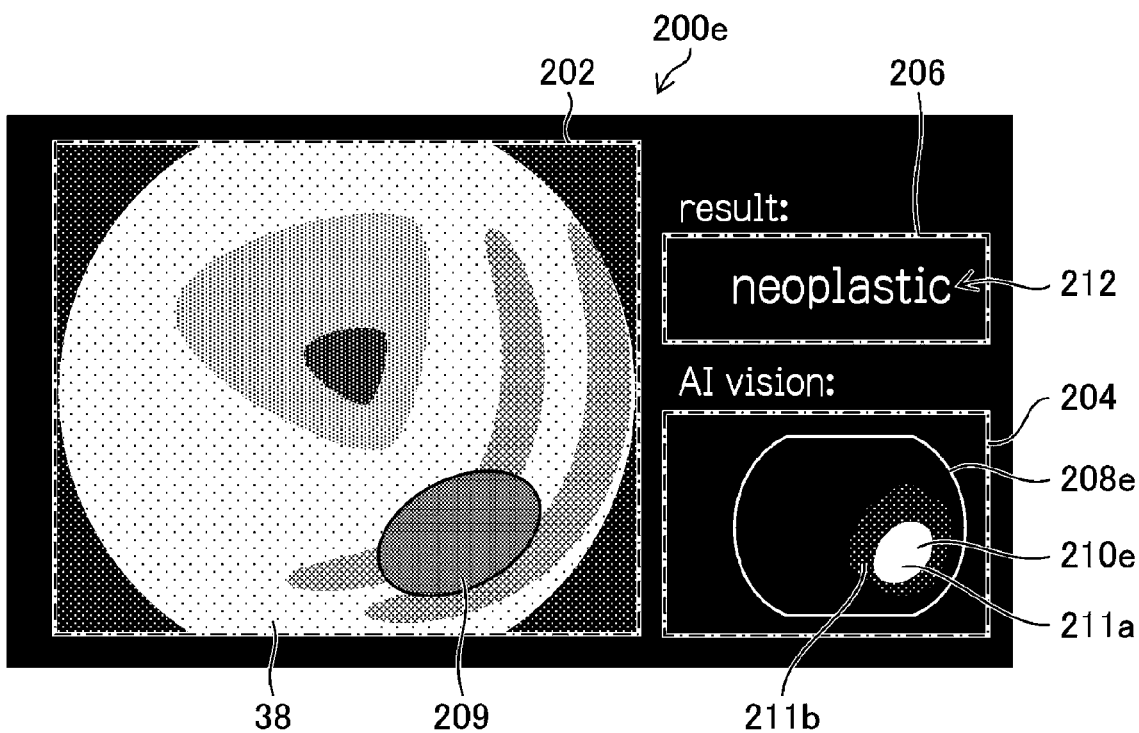
FIG. 16 is an explanatory diagram of a region image to which density according to a degree of contribution is applied.

Display Examples of Region Image According to Degree of Contribution to Classification FIG. 16 is an explanatory diagram of a region image to which density according to a degree of contribution is applied. In the display screen 200e illustrated in FIG. 16, the density according to the degree of contribution is applied to a classification contribution corresponding region 210e in a region image 208e.

In the classification contribution corresponding region 210e illustrated in FIG. 16, a central portion 211a is colored deeper and a peripheral portion 211b is colored lighter. This indicates that the central portion 211a has a high degree of contribution, and the peripheral portion 211b has a low degree of contribution. Note that the degree of contribution may be classified in there or more levels.

Figure 17:
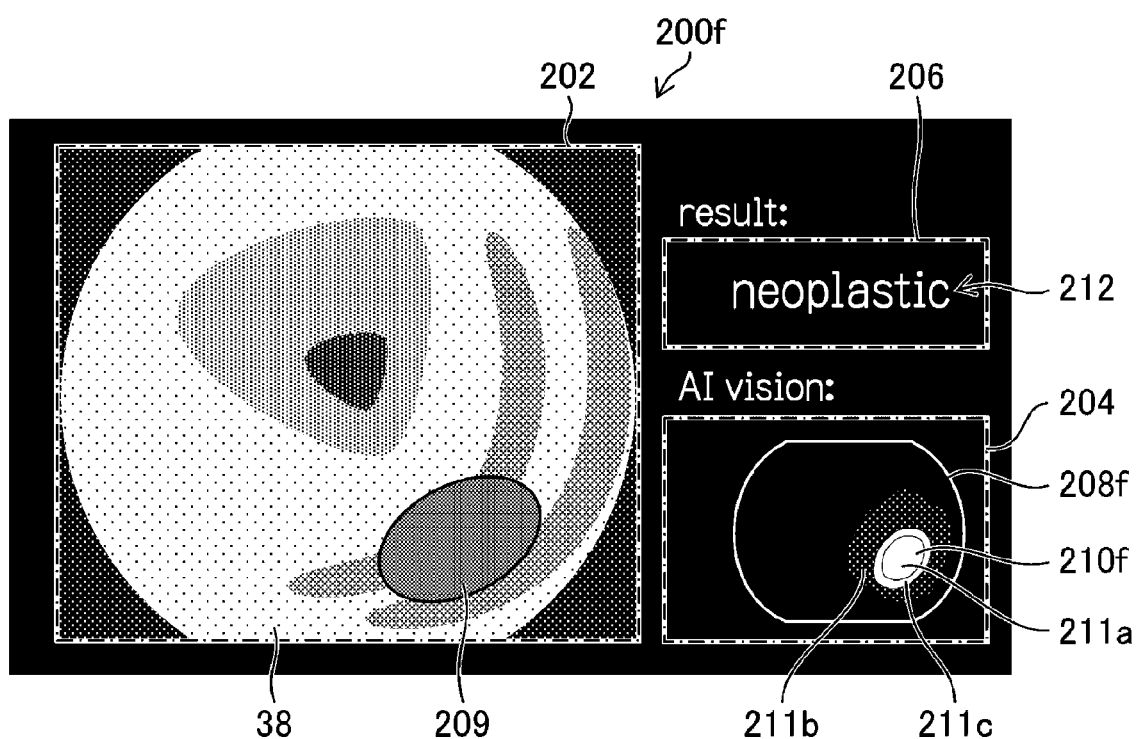
FIG. 17 is an explanatory diagram of a region image to which a heat map according to the degree of contribution is applied.

FIG. 17 is an explanatory diagram of a region image to which a heat map according to the degree of contribution is applied. In the display screen 200f illustrated in FIG. 17, a heat map according to the degree of contribution is applied to a classification contribution corresponding region 210f in a region image 208f.

In the classification contribution corresponding region 210f illustrated in FIG. 17, red is used for the central portion 211a and blue is used for the peripheral portion 211b. An intermediate color that changes from red to blue is used for an intermediate region 211c between the central portion 211a and the peripheral portion 211b. Examples of the intermediate color include orange, yellow, green, and so on.

The classification contribution corresponding region 210f illustrated in FIG. 17 indicates that the degree of contribution of the central portion 211a is high, the degree of contribution decreases from the central portion 211a toward the peripheral portion 211b, and the degree of contribution of the peripheral portion 211b is the lowest. Note that two or more of the modifications described herein may be appropriately combined with one another.

Detailed Description of Classification and Depiction of Region that Contributes to Classification A specific example of classification of the endoscopic image 38 and depiction of a region that contributes to the classification will be described next.

Pattern 1

As a pattern 1, an example is presented in which a feature quantity is calculated from the endoscopic image 38, classification is performed on the basis of the feature quantity, and a region that contributes to the classification is depicted. A method based on a support vector machine (SVM) or the like may be used in the classification based on the feature quantity. For example, a blood vessel region is extracted from the endoscopic image 38, and a feature quantity of the extracted blood vessel region is calculated.

Other methods include a method of performing texture analysis on the endoscopic image 38 and calculating a feature quantity using the analysis result, a method of calculating a local feature quantity such as scale-invariant feature transform (SIFT), and so on.

The feature quantity calculated using any of the aforementioned methods is analyzed in units of regions obtained in the case where the target image is divided into a plurality of regions. In this way, the class membership probability can be calculated in units of regions. This consequently enables depiction processing to be performed for individual regions based on the respective class membership probabilities in units of regions. The plurality of regions described in the embodiments are an example of a plurality of regions set in a captured image.

Pattern 2

As a pattern 2, an example is presented in which information of an intermediate layer of a convolutional neural network is analyzed to classify the endoscopic image 38 and a region that contributes to the classification is depicted. Such a method enables classification and depiction to be processed in parallel.

Figure 18:
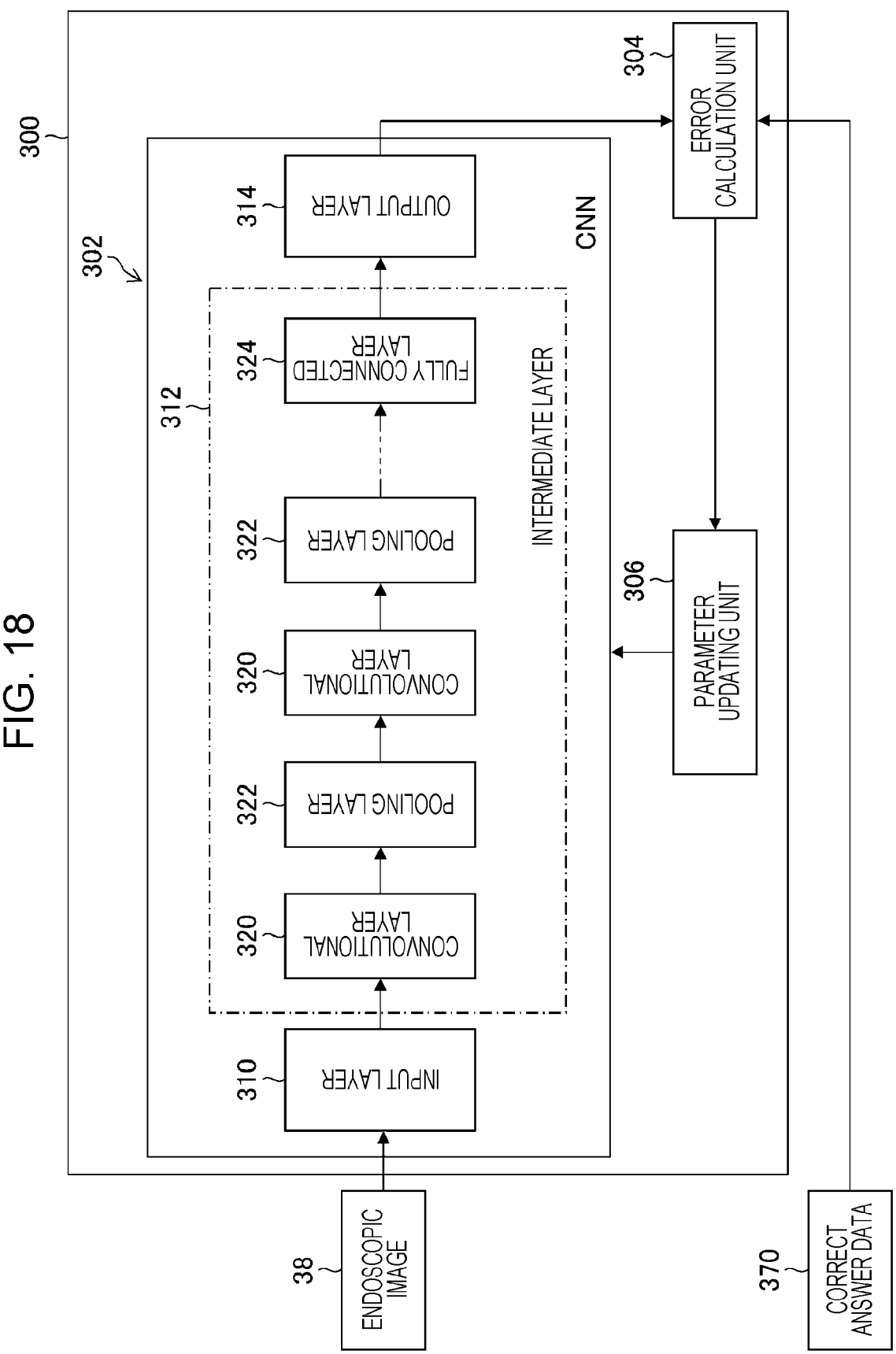
FIG. 18 is a block diagram illustrating an example of a configuration of a classification unit that employs a convolutional neural network.

FIG. 18 is a block diagram illustrating an example of a configuration of a classification unit that employs a convolutional neural network. Hereinafter, the convolutional neural network may be abbreviated as CNN. The classification unit that employs the convolutional neural network described in the embodiments is an example of a deep learning device.

A classification unit 300 illustrated in FIG. 18 is an example of the classification unit 48 illustrated in FIG. 3. The classification unit 300 includes a CNN 302, an error calculation unit 304, and a parameter updating unit 306.

The CNN 302 performs image recognition on the type of a lesion contained in the endoscopic image 38. The CNN 302 has a structure of a plurality of layers and holds a plurality of weight parameters. The weight parameters of the CNN 302 are updated from the initial values to the optimum values. This may change an untrained model to a trained model.

The CNN 302 includes an input layer 310, an intermediate layer 312, and an output layer 314. The intermediate layer 312 includes a plurality of sets of a convolutional layer 320 and a pooling layer 322. The intermediate layer 312 also includes a fully connected layer 324. Each layer is structured such that a plurality of nodes are connected to one another by edges.

The endoscopic image 38 serving as a target to be learned is input to the input layer 310. The intermediate layer 312 extracts features from the endoscopic image 38 input thereto from the input layer 310. The convolutional layer 320 performs filtering processing on nearby nodes in the previous layer to acquire a feature map. Note that the filtering processing is synonymous with a convolution operation using a filter.

The pooling layer 322 reduces the size of the feature map output from the convolutional layer 320 to generate a new feature map. The convolutional layer 320 plays a role of extracting features, such as extracting edges, from the endoscopic image 38.

The pooling layer 322 plays a role of providing robustness so that the extracted features are not affected by translation or the like. Note that the intermediate layer 312 is not limited to the case where the convolutional layer 320 and the pooling layer 322 constitute a single set, and the case where the convolutional layers 320 are consecutively arranged and a configuration including a normalization layer (not illustrated) are also possible.

The output layer 314 classifies the type of the lesion contained in the endoscopic image 38 on the basis of the features extracted using the intermediate layers 312. The trained CNN 302 may classify, for example, a medical image into two classes, that is, a tumor or a non-tumor. The recognition result may be obtained as two kinds of scores corresponding to the tumor or the non-tumor.

Any initial values are set for the coefficient and the offset value of the filter used in the convolutional layer 320 and the connection weight to the next layer of the fully connected layer 324 in the CNN 302 that has not been trained yet.

The error calculation unit 304 acquires the recognition result output from the output layer 314 of the CNN 302 and correct answer data 370 for the endoscopic image 38, and calculates an error therebetween. Examples of the error calculation method include the softmax cross entropy, the sigmoid, and the like.

The parameter updating unit 306 adjusts the weight parameters of the CNN 302 by applying backpropagation based on the error calculated using the error calculation unit 304. The parameter updating unit 306 repeatedly performs the parameter adjustment processing and repeatedly performs training until the difference between the output of the CNN 302 and the correct answer data 370 becomes small.

The classification unit 300 performs training for optimizing each parameter of the CNN 302 by using a data set of the endoscopic images 38 stored in a database (not illustrated) to generate a trained model.

Figure 19:
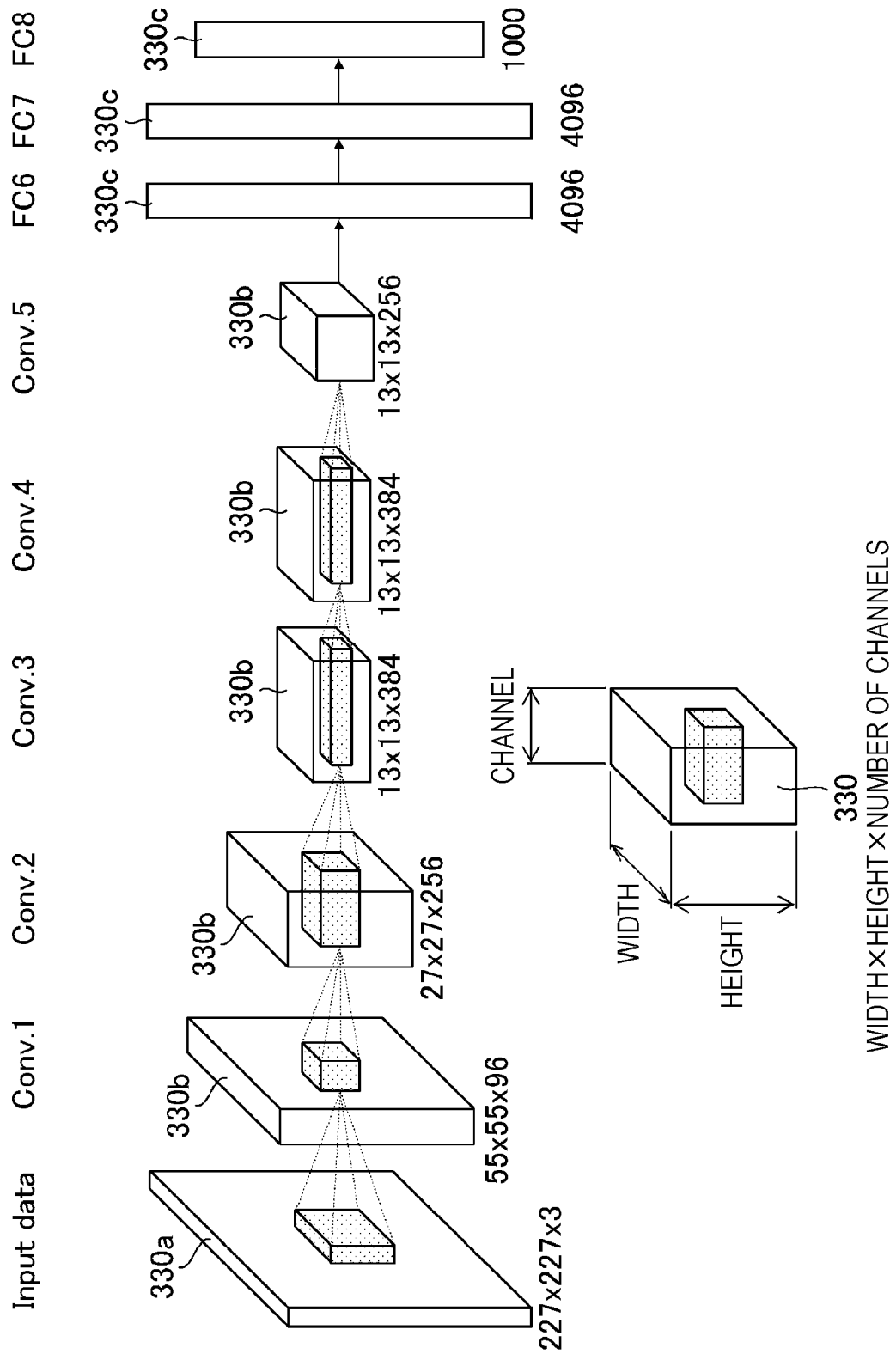
FIG. 19 is a conceptual diagram of the shape transition of a feature quantity in the convolutional neural network.

FIG. 19 is a conceptual diagram of the shape transition of the feature quantity in the convolutional neural network. A reference sign 330 denotes schematized information. Input data represents information 330a of the input layer 310. Conv.1 to Conv.5 represent the intermediate layer 312. FC6 to FC8 represent the fully connected layer 324. In FIG. 19, an information amount of the information 330a of the input layer 310 and an information amount of information 330b of the intermediate layer 312 are represented as width×height× number of channels.

The convolutional neural network performs final output while aggregating spatial information of an input image. As illustrated in FIG. 19, the convolutional neural network aggregates spatial information having a width and a height as the processing advances from the input layer 310 to the intermediate layer 312. Consequently, the spatial information is lost in information 330c of the fully connected layer 324 and thereafter.

That is, analysis of the information 330b of the intermediate layer 312 enables a feature retaining spatial information to be extracted. However, in general, the number of channels of the information 330b of the intermediate layer 312 is larger than that of the information 330a of the input layer 310.

In the example illustrated in FIG. 19, the number of channels of the information 330a is three in the input layer 310, whereas the number of channels of the information 330b is increased to 384 in Conv. 4 of the intermediate layer 312. Accordingly, how to aggregate the information in the channel direction to depict the classification contribution region becomes an issue. Examples in which information in the channel direction is aggregated to depict the classification contribution region will be described below.

First Example

In general, a channel that greatly contributes to the final output tends to have a large absolute value. Accordingly, the absolute values of information in the respective channels of the intermediate layer 312 are compared with each other, and a channel having a larger absolute value is extracted. The extracted channel is depicted. This enables a region that contributes more to the final output to be depicted.

When the channel is extracted, a plurality of channels may be extracted. As an example of the case where a plurality of channels are extracted, there is an example in which a predetermined number of channels are extracted in descending order of the absolute values. When a plurality of channels are extracted, the plurality of channels may be averaged.

Second Example

Principal component analysis may be performed in the channel direction of the intermediate layers 312 to extract a principal component, and the extracted principal component may be depicted. For example, the extracted principal component can be depicted by reducing the dimensions of the channels to one dimension. In the second example, since information of all channels is depicted, more accurate depiction than that in the first example is possible.

Third Example

The final output result is a score for each class label of the classification. The degree of contribution to the score of each class label of the classification can be derived using differentiation. For example, Gradient-weighted Class Activation Mapping (Grad-CAM) may be used to derive the degree of contribution to the score of each class label of the classification.

Let $y^c$ denote the score of an arbitrary class c. Let $A^k$ denote a feature map of a k-th channel of an arbitrary intermediate layer. Let $A^k_{ij}$ denote the values of the coordinates (i, j) of the feature map $A^k$. A map $L^c$Grad-CAM in which the degree of contribution of the class c is depicted is obtained by Equation below.

$$L^c_{Grad-CAM} = ReLU\left(\sum_k \alpha^c_k A^k\right)$$

$$\alpha^c_k = \frac{1}{Z}\sum_i \sum_j \frac{\partial y^c}{\partial A^k_{ij}}$$

$$Z = \sum_i \sum_j 1$$

$$ReLU(x) = \max\{x, 0\}$$

The map $L^c$Grad-CAM represents a region image depicting the classification contribution region in which information in the channel direction is aggregated.

FIG. 20 is a conceptual diagram of depiction based on information of an intermediate layer of a convolutional neural network. The example illustrated in FIG. 20 presents an example in which an image to be processed 380 including two kinds of animals is classified into one animal 381a or another animal 381b and a region serving as a basis of the classification is depicted.

A first classified image 382 presents an example in which the image to be processed 380 is classified into the one animal 381a and a region 384 serving as the basis of the classification is depicted. A second classified image 386 presents an example in which the image to be processed 380 is classified into the other animal 381b and a region 388 serving as the basis of the classification is depicted.

When the pattern 2 is used in classification of the endoscopic image 38, the image to be processed 380 may be replaced with the endoscopic image 38, and the two kinds of animals may be replaced with two kinds of classes. The two kinds of animals may be replaced with two kinds of feature regions.

Pattern 3

Figure 21:
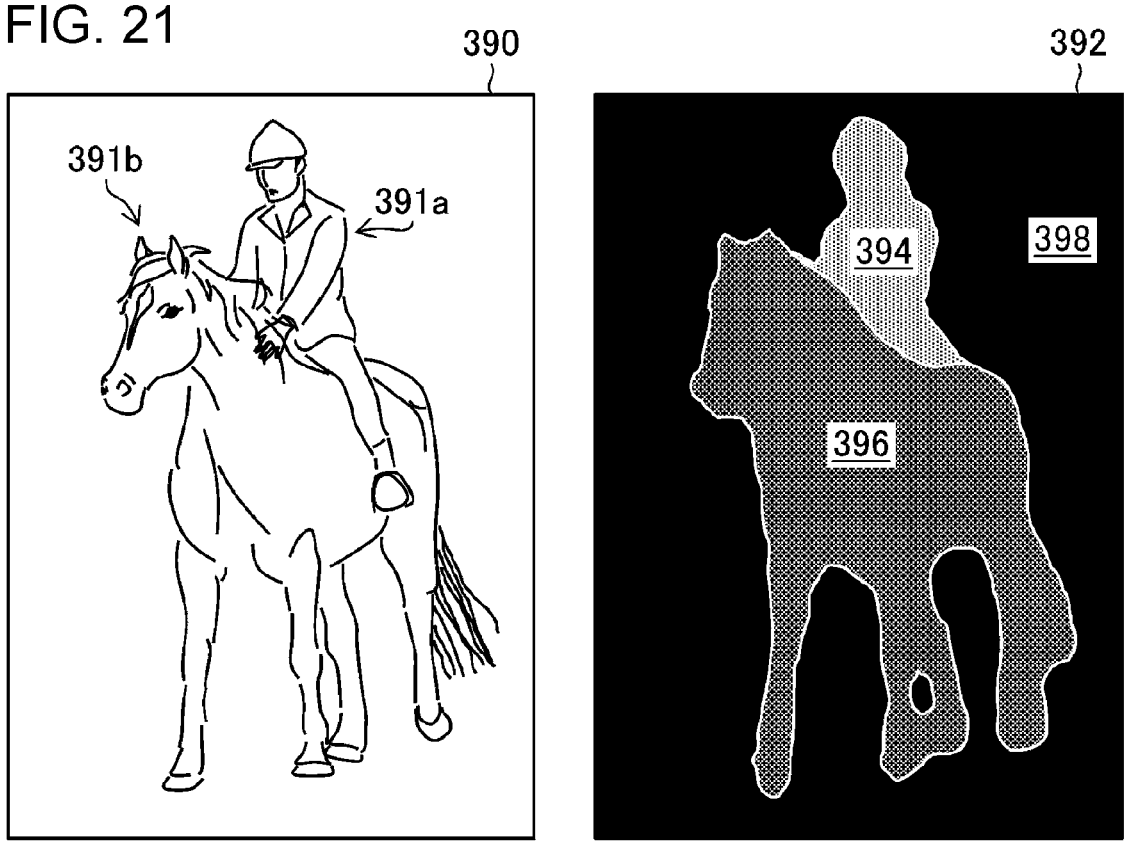
FIG. 21 is an explanatory diagram of a segmentation technique.

As a pattern 3, an example is presented in which a region is depicted using a segmentation technique. FIG. 21 is an explanatory diagram of the segmentation technique. FIG. 21 illustrates an example in which an image to be classified 390 including a person 391a and an animal 391b is classified into a person region 394, an animal region 396, and a background region 398. A reference sign 392 denotes a classified image.

With the segmentation technique, a class membership probability is obtained for each region. Each region can be depicted based on the membership probability. Classification can be performed on the image to be classified 390 on the basis of the regions obtained using the segmentation technique. For example, a class having the largest area in the image to be classified 390 among the classes used in classification may be set as the classification result.

Advantageous Effects of First Embodiment

With the medical image processing apparatus according to the first embodiment, the following advantageous effects can be obtained.

[1] The endoscopic image 38 is displayed in the endoscopic image display area 202 of the display screen 200 displayed on the monitor device 16. The region image 208 is displayed in the region image display area 204 different from the endoscopic image display area 202 of the display screen 200. The region image 208 includes the classification contribution corresponding region 210 corresponding to the classification contribution region 209 that contributes to classification of the endoscopic image 38. This allows an observer to visually grasp which region in the endoscopic image 38 the classification unit 48 performs classification on the basis of. In addition, the region image 208 may serve as an index of the reliability of the classification result.

[2] The classification result is displayed on the monitor device 16. This allows the observer to visually recognize the classification result of the endoscopic image 38.

[3] A membership degree for each class is derived as the classification result. The membership degree of each class is displayed on the monitor device 16. As the membership degree, a membership probability for each class or a score for each class may be used. This allows the observer to visually recognize the membership degree for each class.

[4] A display manner of the region image 208 may be changed in accordance with the classification result. This may improve the visibility of the classification result.

Description of Medical Image Processing Apparatus According to Second Embodiment A medical image processing apparatus according to a second embodiment will be described next. In the medical image processing apparatus according to the second embodiment, exception determination is added to classification of the endoscopic image 38. That is, a lesion region of the endoscopic image 38 is depicted using the pattern 1, the pattern 2, and the pattern 3 described in the first embodiment, and then the region image is analyzed to make exception determination.

For example, if the area of the lesion region detected from the endoscopic image 38 is equal to or less than a predetermined threshold value, the classification result may be set as undetectable. If there are a plurality of lesion regions detected from the endoscopic image 38 and the areas of all the lesion regions are equal to or greater than a predetermined threshold value, the classification result may be set as undeterminable.

Note that the medical image processing apparatus according to the second embodiment employs substantially the same hardware and functional blocks as those of the medical image processing apparatus 14 according to the first embodiment. Thus, description of the hardware and functional blocks of the medical image processing apparatus according to the second embodiment will be omitted.

Display Screen Displayed in Case of Being Undetectable

Figure 22:
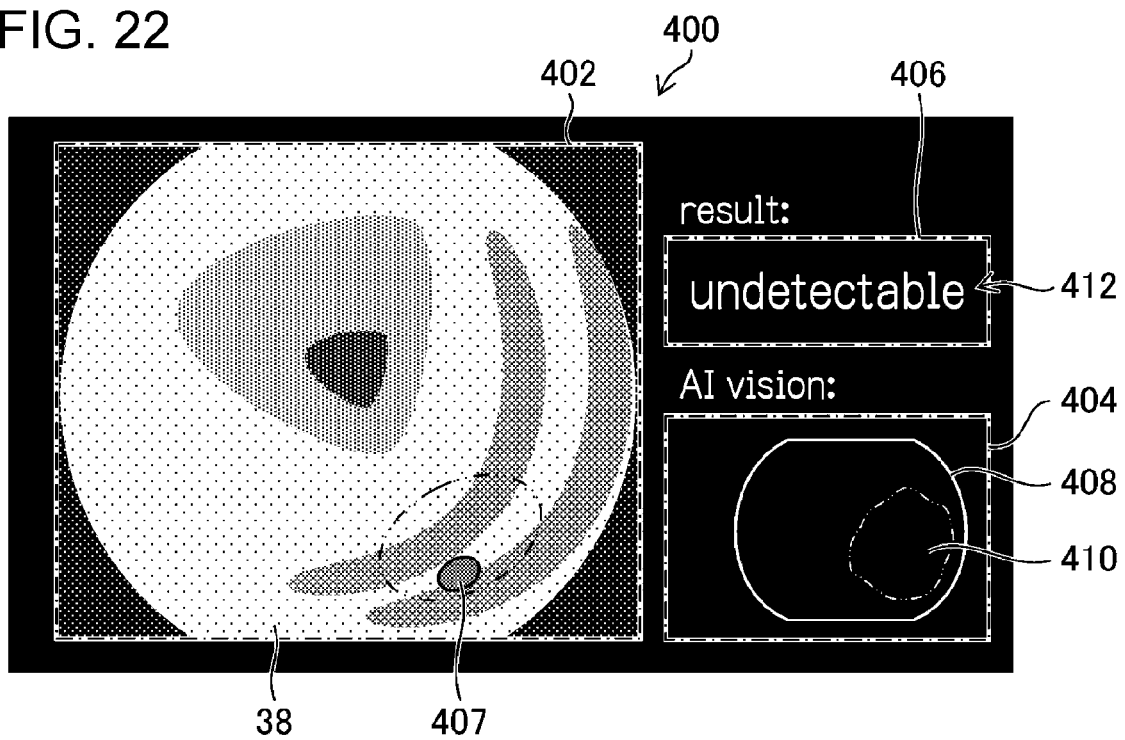
FIG. 22 is an explanatory diagram of a display screen indicating the classification result of "undetectable"

FIG. 22 is an explanatory diagram of a display screen indicating the classification result of "undetectable". In a display screen 400 illustrated in FIG. 22, undetectable indicating the classification result of "undetectable" is displayed as text information 412. When the text information 412 representing undetectable is displayed, a classification contribution corresponding region 410 is not displayed in a region image 408. Note that FIG. 22 schematically illustrates, using a solid line, a lesion region 407 that is undetectable. The lesion region 407 that is detectable is schematically illustrated using a two-dot chain line.

A configuration in which the text information representing the classification result is overwritten with text information representing undetectable may be used as the text information 412. The display screen 400 may employ a configuration indicating that the lesion is undetectable, separately from the text information indicating the classification result.

The classification unit 48 illustrated in FIG. 3 may analyze the region image 408 to quantify the degree of reliability of the classification. The display control unit 44 may display a numerical value such as a score representing the degree of reliability of the classification in the display screen 400. Note that a reference sign 402 illustrated in FIG. 22 denotes the endoscopic image display area. A reference sign 404 denotes the region image display area. A reference sign 406 denotes the classification result display area.

Display Screen Displayed in Case of Being Undeterminable

Figure 23:
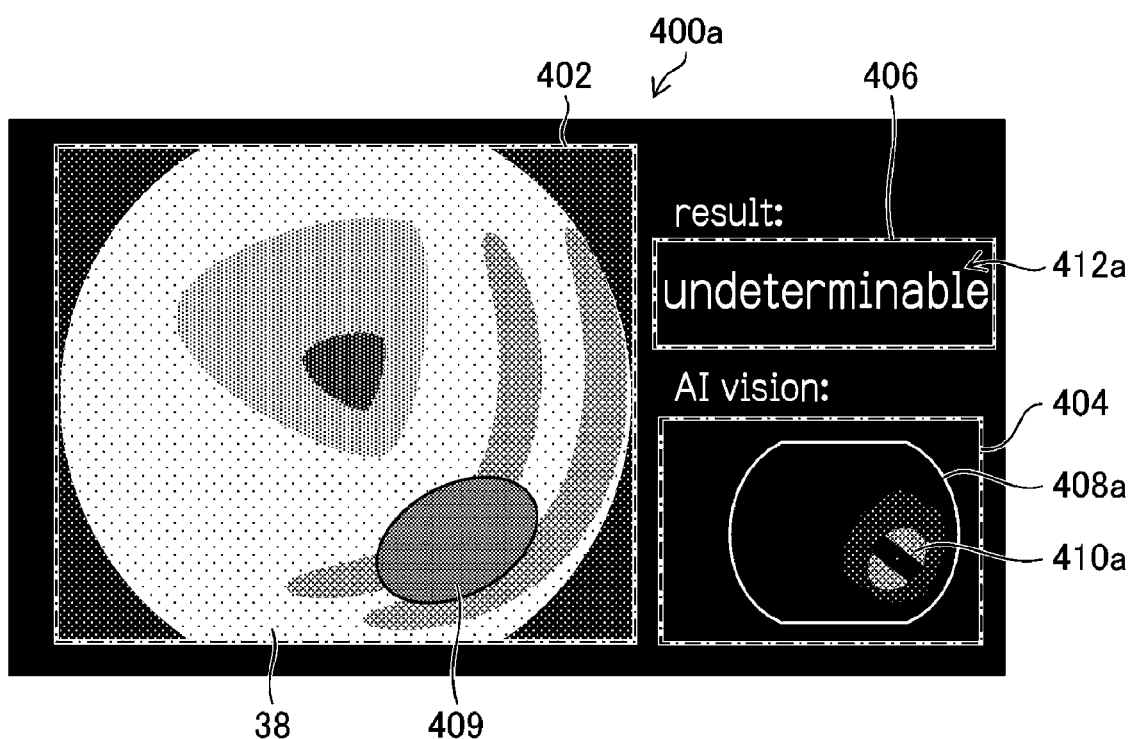
FIG. 23 is an explanatory diagram of a display screen indicating the classification result of "undeterminable"

FIG. 23 is an explanatory diagram of a display screen indicating the classification result of "undeterminable". In a display screen 400a illustrated in FIG. 23, undeterminable indicating the classification result of "undeterminable" is displayed as text information 412a. When the text information 412a representing undeterminable is displayed, a classification contribution corresponding region 410a indicating the undeterminable state is displayed in a region image 408a.

Examples of the classification contribution corresponding region 410a indicating the undeterminable state include an example in which two types of display manners corresponding to different classifications coexist. FIG. 23 illustrates the classification contribution corresponding region 410a in which two colors coexist in the case where the color is changed in accordance with the classification. Note that a reference sign 409 in FIG. 23 denotes the classification contribution region.

Advantageous Effects of Second Embodiment

With the medical image processing apparatus according to the second embodiment, the following advantageous effects can be obtained.

[1] When a lesion in the endoscopic image 38 is undetectable, the text information 412 indicating that the lesion is undetectable is displayed. When a lesion in the endoscopic image 38 is undeterminable, the text information 412 indicating that the lesion is undeterminable is displayed. This allows the operator to grasp the inappropriate classification.

[2] The degree of reliability of classification is calculated on the basis of the region image. The degree of reliability is displayed in the display screen. This enables the degree of reliability of classification to be recognized.

Description of Medical Image Processing Apparatus According to Third Embodiment

Figure 24:
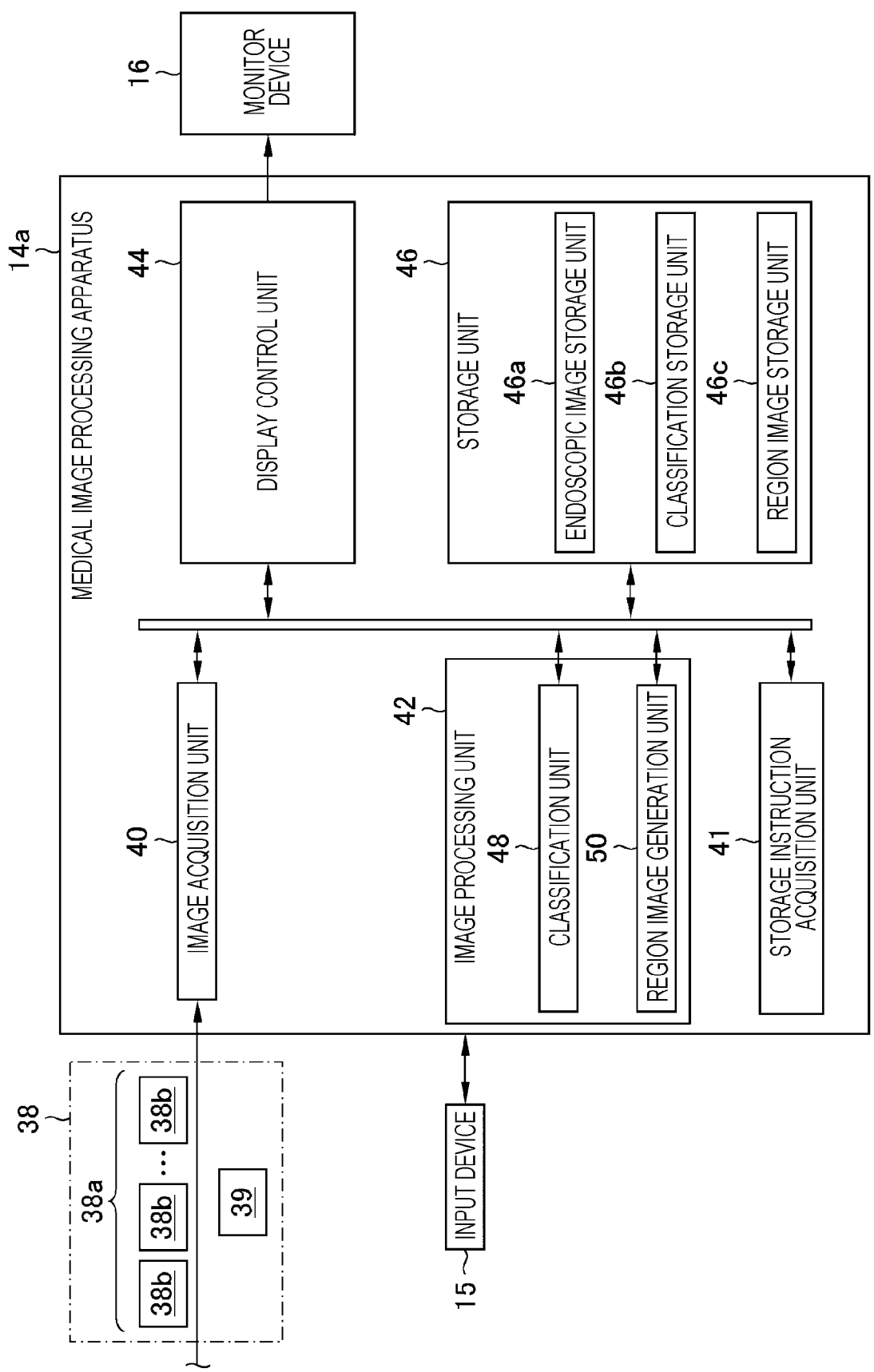
FIG. 24 is a functional block diagram of a medical image processing apparatus according to a third embodiment.

FIG. 24 is a functional block diagram of a medical image processing apparatus according to a third embodiment. A medical image processing apparatus 14a illustrated in FIG. 24 includes a storage instruction acquisition unit 41, compared to the medical image processing apparatus 14 illustrated in FIG. 3. The storage instruction acquisition unit 41 acquires an instruction to store the endoscopic image 38, transmitted from the processor device 12 illustrated in FIG. 1. The storage instruction acquisition unit 41 may acquire the instruction to store the endoscopic image 38 from the endoscope 10.

In response to the storage instruction acquisition unit 41 acquiring the instruction to store the endoscopic image 38, the endoscopic image 38 acquired using the image acquisition unit 40 is stored in the endoscopic image storage unit 46a in association with at least any of the classification result, the region image, the exception determination result, or the degree of reliability.

The medical image processing apparatus 14a may combine the classification result and the like with the endoscopic image 38 and store the combined result, or may separately store the classification result and the like and the endoscopic image 38. In response to the operator operating an operation button (not illustrated) or the like, the instruction to store the endoscopic image 38 may be transmitted from the processor device 12. Alternatively, the instruction to store the endoscopic image 38 may be automatically transmitted from the processor device 12 on the basis of the classification result or the like. When the degree of reliability is equal to or higher than a predetermined threshold value, the processor device 12 may determine that the medical image processing apparatus 14a has obtained an appropriate classification result and automatically transmit the instruction to store the endoscopic image 38.

Advantageous Effects of Third Embodiment

With the medical image processing apparatus according to the third embodiment, the following advantageous effects can be obtained.

[1] When a user creates a report after an endoscopic examination, the user may check whether the classification result or the like is appropriate.

[2] At the time of re-examination, examination results of the preceding examinations may be referred to.

Modifications of Endoscope System

Modification of Processor Device

The processor device 12 may have the functions of the medical image processing apparatus 14. That is, the processor device 12 and the medical image processing apparatus 14 may be integrated together. In such an embodiment, the display device 13 may also serve as the monitor device 16. The processor device 12 may include a connection terminal to which the input device 15 is connected.

Modification of Illumination Light

One example of the medical image acquirable using the endoscope system 9 according to the present embodiments is a normal-light image acquired by radiating light in a white range or light in a plurality of wavelength ranges as the light in the white range.

Another example of the medical image acquirable using the endoscope system 9 according to the present embodiments is an image acquired by radiating light in a specific wavelength range. A range narrower than the white range may be used as the specific wavelength range. The following modifications may be employed.

First Example

A first example of the specific wavelength range is a blue range or a green range in a visible range. The wavelength range of the first example includes a wavelength range of 390 nm or more and 450 nm or less or a wavelength range of 530 nm or more and 550 nm or less, and the light of the first example has a peak wavelength in the wavelength range of 390 nm or more and 450 nm or less or the wavelength range of 530 nm or more and 550 nm or less.

Second Example

A second example of the specific wavelength range is a red range in the visible range. The wavelength range of the second example includes a wavelength range of 585 nm or more and 615 nm or less or a wavelength range of 610 nm or more and 730 nm or less, and the light of the second example has a peak wavelength in the wavelength range of 585 nm or more and 615 nm or less or the wavelength range of 610 nm or more and 730 nm or less.

Third Example

A third example of the specific wavelength range includes a wavelength range in which an absorption coefficient is different between oxyhemoglobin and deoxyhemoglobin, and the light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or more and 750 nm or less, and the light of the third example has a peak wavelength in the wavelength range of 400±10 nm, the wavelength range of 440±10 nm, the wavelength range of 470±10 nm, or the wavelength range of 600 nm or more and 750 nm or less.

Fourth Example

A fourth example of the specific wavelength range is a wavelength range of excitation light that is used to observe fluorescence emitted by a fluorescent substance in a living body and excites this fluorescent substance. For example, the specific wavelength range of the fourth example is a wavelength range of 390 nm or more and 470 nm or less. Note that observation of fluorescence may be referred to as fluorescence observation.

Fifth Example

A fifth example of the specific wavelength range is a wavelength range of infrared light. The wavelength range of this fifth example includes a wavelength range of 790 nm or more and 820 nm or less or a wavelength range of 905 nm or more and 970 nm or less, and the light of the fifth example has a peak wavelength in the wavelength range of 790 nm or more and 820 nm or less or the wavelength range of 905 nm or more and 970 nm or less.

Generation Example of Special-Light Image

The processor device 12 may generate a special-light image having information in the specific wavelength range on the basis of a normal-light image obtained through imaging using white light. Note that the term "generation" used herein includes "acquisition". In this case, the processor device 12 functions as a special-light image acquisition unit. The processor device 12 obtains a signal of the specific wavelength range by performing calculation based on color information of red, green, and blue or color information of cyan, magenta, and yellow included in the normal-light image.

Note that red, green, and blue are sometimes referred to as RGB. In addition, cyan, magenta, and yellow are sometimes referred to as CMY.

Generation Example of Feature-Quantity Image

As the medical image, a feature-quantity image may be generated by using an operation based on at least any of a normal-light image obtained by radiating light in the white range or light in a plurality of wavelength ranges as the light in the white range or a special-light image obtained by radiating light in the specific wavelength range.

Application Example to Program for Causing Computer to Function as Image Processing Apparatus The above-described image processing method can be configured as a program that implements functions corresponding to respective steps of the image processing method using a computer. For example, a program that causes a computer to implement an endoscopic image acquisition function, an image processing function, a display signal transmission function, and a storage function may be configured. The image processing functions may include a classification function and a region image generation function.

A program that causes a computer to implement the above-described image processing function may be stored on a computer-readable information storage medium which is a non-transitory tangible information storage medium, and the program may be provided using the information storage medium.

In addition, instead of the configuration in which the program is stored on a non-transitory information storage medium and is provided, a configuration in which a program signal is provided via a network may be employed.

Combination of Embodiments, Modifications, etc.

The constituent elements described in the embodiments above and the constituent elements described in the modifications can be appropriately used in combination, and some of the constituent elements can be replaced.

Application Examples to Other Devices

In the embodiments described above, an endoscopic image is used as an example of a medical image. However, automatic classification described in the present embodiments is also applicable to a medical image acquired using a CT apparatus, an MRI apparatus, an X-ray imaging apparatus, or the like. The medical image described in the embodiments is an example of a captured image.

In the embodiments of the present invention described above, the constituent elements can be appropriately changed, added, or deleted within a scope not departing from the gist of the present invention. The present invention is not limited to the embodiments described above, and various modifications can be made by a person having the ordinary skill in the art within the technical sprit of the present invention.

REFERENCE SIGNS LIST 9 endoscope system
10 endoscope 11 light source device
12 processor device
13 display device
14 medical image processing apparatus
14a medical image processing apparatus
15 input device
16 monitor device
20 insertion section
21 operation section
22 universal cord
25 soft part
26 bending part
27 tip part
27a tip surface
28 imaging element
29 bending operation knob
30 air/water supply button
31 suction button
32 still image capturing instruction part
33 treatment tool introduction port
35 light guide
36 signal cable
37a connector
37b connector
38 endoscopic image
38a moving image
38b frame image
39 still image
40 image acquisition unit
41 storage instruction acquisition unit
42 image processing unit
44 display control unit
46 storage unit
46a endoscopic image storage unit
46b classification storage unit
46c region image storage unit
48 classification unit
50 region image generation unit
120 control unit
122 memory
124 storage device
126 network controller
128 power supply device
130 display controller
132 input/output interface
134 input controller
136 bus
140 network
200 display screen
200a display screen
200b display screen
200c display screen
200d display screen
200e display screen
201 frame
202 endoscopic image display area
204 region image display area
206 classification result display area
206a classification result display area
207 frame
208 region image
208a region image
208b region image
208c region image
208d region image
208e region image
208f region image
208g region image
208h region image
209 classification contribution region
209a first classification contribution region
209b second classification contribution region
210 classification contribution corresponding region
210a region to be set as classification contribution corresponding region
210b region to be set as classification contribution corresponding region
210e classification contribution corresponding region
210f classification contribution corresponding region
210g first classification contribution corresponding region
210h second classification contribution corresponding region
211a central portion
211b peripheral portion
211c intermediate region
212 text information
212a text information
212b text information
212c text information
212d text information
212e first text information
212f second text information
213a first lesion
213b second lesion
220 comparative screen
222 tumor
230 region
300 classification unit
302 CNN
304 error calculation unit
306 parameter updating unit
310 input layer
312 intermediate layers
314 output layer
320 convolutional layer
322 pooling layer
324 fully connected layer
330 information
330a information of input layer
330b information of intermediate layer
330c information of fully connected layer
370 correct answer data
380 image to be processed
381a one animal
381b another (other) animal
382 first classified image
384 region serving as basis of classification
386 second classified image
388 region serving as basis of classification
390 image to be classified
391a person
391b animal
392 classified image
394 person region
396 animal region
400 display screen
400a display screen
402 endoscopic image display area
404 region image display area
406 classification result display area
408 region image
410 classification contribution corresponding region
412 text information
412a text information
S10 to S22 steps of medical image processing method

What is claimed is:

1. A medical image processing apparatus comprising one or more processors configured to:
   acquire an endoscopic image generated through imaging of a living body;
   perform classification of lesion regions contained in the endoscopic image into two or more classes representing types of lesions, the types including a type specifying a first lesion and a type specifying a second lesion, the first lesion and the second lesion being different from each other in type;
   identify a classification contributing region in the endoscopic image, the classification contributing region contributing to the classification of one of the lesion regions contained in the endoscopic image;
   generate a region image displaying a region in the endoscopic image, the region image displaying the region corresponding to the classification contributing region in a display manner different in accordance with a result of the classification of the one of the lesion regions; and
   display the region image along with the endoscopic image on a monitor, a region image being displayed at a position different from a position at which the endoscopic image is displayed.

2. The medical image processing apparatus according to claim 1, wherein the one or more processors are configured to
   perform the classification of the endoscopic image on the basis of a feature quantity acquired from the endoscopic image, and
   generate the region image on the basis of the feature quantity.

3. The medical image processing apparatus according to claim 1, wherein the one or more processors are configured to
   employ a deep learning device that has been trained, and
   generate the region image on the basis of information of an intermediate layer of the deep learning device.

4. The medical image processing apparatus according to claim 1, wherein the one or more processors are configured to
   calculate, for each of a plurality of regions set in the endoscopic image, membership degrees for the classes, and
   classify the endoscopic image on the basis of the membership degrees.

5. The medical image processing apparatus according to claim 4, wherein the one or more processors are configured to generate the region image on the basis of the membership degrees.

6. The medical image processing apparatus according to claim 1, wherein the one or more processors are configured to
   perform exception determination for the classification based on the region image, and
   cause the monitor to display a result of the exception determination.

7. The medical image processing apparatus according to claim 6, wherein the one or more processors are configured to
   calculate, on the basis of the region image, a degree of reliability of the result of the classification, and
   cause the monitor to display the degree of reliability.

8. The medical image processing apparatus according to claim 7, further comprising:
   a memory configured to store the endoscopic image,
   wherein the one or more processors are configured to
   acquire an instruction to store the endoscopic image in the memory, and
   associate, in storing the endoscopic image in the memory in accordance with the instruction to store the endoscopic image, at least any of the result of the classification, the result of the exception determination, or the degree of reliability of the result of the classification with the endoscopic image.

9. The medical image processing apparatus according to claim 1, wherein the one or more processors are configured to cause the monitor to display text information of the result of the classification.

10. The medical image processing apparatus according to claim 1, wherein the one or more processors are configured to, in a case where the one of the lesion regions is classified into a first one of the classes representing the first lesion, generate the region image displaying the region corresponding to the classification contributing region in a first display manner.

11. The medical image processing apparatus according to claim 1, wherein the one or more processors are configured to, in a case where the one of the lesion regions is classified into a second one of the classes representing the second lesion, generate the region image displaying the region corresponding to the classification contributing region in a second display manner.

12. The medical image processing apparatus according to claim 1, wherein the one or more processors are configured to, in a case where two or more of the lesion regions are classified into a first one of the classes representing the first lesion and a second one of the classes representing the second lesion, generate the region image displaying the region corresponding to the classification contributing region contributing to the classification of the first one of the classes in a first display manner, and displaying the region corresponding to the classification contributing region contributing to the classification of the second one of the classes in a second display manner.

13. The medical image processing apparatus according to claim 1, wherein:
   the one or more processors are configured to perform the classification of the lesion regions contained in the endoscopic image into a neoplastic lesion and a non-neoplastic lesion; and
   one of the first lesion and the second lesion is the neoplastic lesion, and the other of the first lesion and the second lesion is the non-neoplastic lesion.

14. The medical image processing apparatus according to claim 1, wherein the endoscopic image is a normal-light image acquired by radiating light in a white range or light in a plurality of wavelength ranges as the light in the white range.

15. The medical image processing apparatus according to claim 1, wherein the endoscopic image is a special-light image acquired by radiating light in a specific wavelength range.

16. An endoscopy system comprising:
   an endoscope;
   a light source configured to supply illumination light to the endoscope; and
   the medical image processing apparatus according to claim 1,
   wherein the one or more processors acquire the endoscopic image from the endoscope.

17. A medical image processing system comprising one or more processors configured to:

acquire an endoscopic image generated through imaging of a living body;

perform classification of lesion regions contained in the endoscopic image into two or more classes representing types of lesions, the types including a type specifying a first lesion and a type specifying a second lesion, the first lesion and the second lesion being different from each other in type;

identify a classification contributing region in the endoscopic image, the classification contributing region contributing to the classification of one of the lesion regions contained in the endoscopic image; and generate a region image displaying a region in the endoscopic image, the region image displaying the region corresponding to the classification contributing region in a display manner different in accordance with a result of the classification of the one of the lesion regions;

wherein the medical image processing system further comprises a monitor configured to display the endoscopic image and the region image, wherein the one or more processors are configured to cause the monitor to display the region image along with the endoscopic image, the region image being displayed at a position different from a position at which the endoscopic image is displayed.

18. A method of operating a medical image processing apparatus, the method comprising:

acquiring an endoscopic image generated through imaging of a living body;

performing classification of lesion regions contained in the endoscopic image into two or more classes representing types of lesions, the types including a type specifying a first lesion and a type specifying a second lesion, the first lesion and the second lesion being different from each other in type;

identifying a classification contributing region in the endoscopic image, the classification contributing region contributing to the classification of one of the lesion regions contained in the endoscopic image;

generating a region image displaying a region in the endoscopic image, the region image displaying the region corresponding to the classification contributing region in a display manner different in accordance with a result of the classification of the one of the lesion regions; and displaying the region image along with the endoscopic image on a monitor, the region image being displayed at a position different from a position at which the endoscopic image is displayed.

19. A non-transitory computer-readable storage medium storing commands that, when read by a computer, cause the computer to:

acquire an endoscopic image generated through imaging of a living body;

perform classification of lesion regions contained in the endoscopic image into two or more classes representing types of lesions, the types including a type specifying a first lesion and a type specifying a second lesion, the first lesion and the second lesion being different from each other in type;

identify a classification contributing region in the endoscopic image, the classification contributing region contributing to the classification of one of the lesion regions contained in the endoscopic image;

generate a region image displaying a region in the endoscopic image, the region image displaying the region corresponding to the classification contributing region in a display manner different in accordance with a result of the classification of the one of the lesion regions; and display the region image along with the endoscopic image on a monitor, the region image being displayed at a position different from a position at which the endoscopic image is displayed.

* * * * *